(12) United States Patent
McDaniel

(10) Patent No.: US 7,494,503 B2
(45) Date of Patent: *Feb. 24, 2009

(54) METHOD AND APPARATUS FOR ACNE PREVENTION

(75) Inventor: David H. McDaniel, Virginia Beach, VA (US)

(73) Assignee: Light BioScience, LLC, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/783,538

(22) Filed: Apr. 10, 2007

(65) Prior Publication Data

US 2007/0191822 A1 Aug. 16, 2007

Related U.S. Application Data

(60) Continuation of application No. 11/119,378, filed on May 2, 2005, now Pat. No. 7,201,765, which is a division of application No. 09/933,870, filed on Aug. 22, 2001, now Pat. No. 6,887,260, which is a continuation-in-part of application No. 09/819,082, filed on Feb. 12, 2001, now abandoned, which is a division of application No. 09/203,178, filed on Nov. 30, 1998, now Pat. No. 6,283,956.

(51) Int. Cl.
*A61N 5/06* (2006.01)

(52) U.S. Cl. ............................. 607/88; 607/89; 606/3; 606/9; 128/898

(58) Field of Classification Search ............. 607/88–91, 607/94; 606/3, 9–11, 13; 128/898

See application file for complete search history.

(56) References Cited

U.S. PATENT DOCUMENTS

| | | | |
|---|---|---|---|
| 3,499,437 | A | 3/1970 | Balamuth |
| 4,458,678 | A | 7/1984 | Yannas et al. |
| 4,558,700 | A | 12/1985 | Mutzhas |
| 4,603,496 | A | 8/1986 | Latz et al. |
| 4,628,422 | A | 12/1986 | Ewald |
| 4,646,743 | A | 3/1987 | Parris |

(Continued)

FOREIGN PATENT DOCUMENTS

EP        0-159-446        10/1985

(Continued)

OTHER PUBLICATIONS

"Hair Regrowth with Cell Wave Therapy," A Guide to Treatment 1996.

(Continued)

*Primary Examiner*—Ahmed M Farah
(74) *Attorney, Agent, or Firm*—Morrison & Foerster LLP

(57) ABSTRACT

Disclosed is a system and method for treating and preventing skin disorders. More particularly, the disclosed invention is directed toward the prevention of acne and acne scarring by treating sebaceous oil glands and the surrounding tissue with an exogenous chromophore composition and then exposing the target tissue to visible, infrared, or ultraviolet light to inhibit the activity of the oil gland and eliminate acne bacteria. The method of the present invention may be further augmented by enhancing the penetration of the topical composition into the oil gland and surrounding tissue through the use of procedures including enzyme peeling, microderm abrasion, or ultrasound.

9 Claims, 13 Drawing Sheets

U.S. PATENT DOCUMENTS

| | | | |
|---|---|---|---|
| 4,753,958 A | 6/1988 | Weinstein et al. | |
| 4,767,402 A | 8/1988 | Kost et al. | |
| 4,822,335 A | 4/1989 | Kawai et al. | |
| 4,836,203 A | 6/1989 | Muller et al. | |
| 4,880,001 A | 11/1989 | Weinberg | |
| 4,888,354 A | 12/1989 | Chang et al. | |
| 4,907,132 A | 3/1990 | Parker | |
| 4,930,504 A | 6/1990 | Diamantopulos et al. | |
| 4,932,934 A | 6/1990 | Dougherty et al. | |
| 4,935,665 A | 6/1990 | Murata | |
| 4,969,912 A | 11/1990 | Kelman et al. | |
| 5,012,609 A | 5/1991 | Ignatius et al. | |
| 5,021,452 A | 6/1991 | Labbe et al. | |
| 5,037,432 A | 8/1991 | Molinari | |
| 5,071,416 A | 12/1991 | Heller et al. | |
| 5,198,465 A | 3/1993 | Dioguardi | |
| 5,226,907 A | 7/1993 | Tankovich | |
| 5,231,975 A | 8/1993 | Bommannan et al. | |
| 5,257,173 A | 10/1993 | Ohmamyuda et al. | |
| 5,259,380 A | 11/1993 | Mendes et al. | |
| 5,262,401 A | 11/1993 | Vogel et al. | |
| 5,266,480 A | 11/1993 | Naughton et al. | |
| 5,278,432 A | 1/1994 | Ignatius et al. | |
| 5,332,802 A | 7/1994 | Kelman et al. | |
| 5,344,434 A | 9/1994 | Talmore | |
| 5,358,503 A | 10/1994 | Bertwell et al. | |
| 5,366,498 A | 11/1994 | Brannan et al. | |
| 5,397,352 A | 3/1995 | Burres | |
| 5,423,803 A | 6/1995 | Tankovich et al. | |
| 5,425,728 A | 6/1995 | Tankovich | |
| 5,445,146 A | 8/1995 | Bellinger | |
| 5,445,608 A | 8/1995 | Chen et al. | |
| 5,445,634 A | 8/1995 | Keller | |
| 5,460,939 A | 10/1995 | Hansbrough et al. | |
| 5,500,009 A | 3/1996 | Mendes et al. | |
| 5,591,444 A | 1/1997 | Boss, Jr. | |
| 5,616,140 A | 4/1997 | Prescott | |
| 5,620,478 A | 4/1997 | Eckhouse | |
| 5,634,711 A | 6/1997 | Kennedy et al. | |
| 5,643,334 A | 7/1997 | Eckhouse et al. | |
| 5,647,866 A | 7/1997 | Zaias et al. | |
| 5,658,323 A | 8/1997 | Miller | |
| 5,660,461 A | 8/1997 | Ignatius et al. | |
| 5,660,836 A | 8/1997 | Knowlton | |
| 5,660,850 A | 8/1997 | Boss, Jr. | |
| 5,665,372 A | 9/1997 | Boss, Jr. | |
| 5,669,916 A | 9/1997 | Anderson | |
| 5,683,380 A | 11/1997 | Eckhouse | |
| 5,686,112 A | 11/1997 | Liedtke | |
| 5,698,866 A | 12/1997 | Doiron et al. | |
| 5,707,401 A | 1/1998 | Talmore | |
| 5,728,090 A | 3/1998 | Martin et al. | |
| 5,752,948 A | 5/1998 | Tankovich | |
| 5,752,949 A | 5/1998 | Tankovich et al. | |
| 5,755,752 A | 5/1998 | Segal | |
| 5,766,214 A | 6/1998 | Mehl, Sr. et al. | |
| 5,766,233 A | 6/1998 | Thiberg | |
| 5,773,609 A | 6/1998 | Robinson et al. | |
| 5,800,478 A | 9/1998 | Chen et al. | |
| 5,810,801 A | 9/1998 | Anderson et al. | |
| 5,817,089 A | 10/1998 | Tankovich et al. | |
| 5,836,999 A | 11/1998 | Eckhouse et al. | |
| 5,843,072 A | 12/1998 | Furumoto et al. | |
| 5,871,480 A | 2/1999 | Tankovich | |
| 5,913,883 A | 6/1999 | Alexander et al. | |
| 5,951,596 A | 9/1999 | Bellinger | |
| 6,030,374 A | 2/2000 | McDaniel | |
| 6,048,301 A | 4/2000 | Sabuda | |
| 6,050,990 A | 4/2000 | Tankovich et al. | |
| 6,063,108 A | 5/2000 | Salansky et al. | |
| 6,074,382 A | 6/2000 | Asah et al. | |
| 6,143,287 A | 11/2000 | Ben-Hur et al. | |
| 6,171,332 B1 | 1/2001 | Whitehurst | |
| 6,183,773 B1 | 2/2001 | Anderson | |
| 6,187,029 B1 | 2/2001 | Shapiro et al. | |
| 6,190,315 B1 | 2/2001 | Kost et al. | |
| 6,190,376 B1 | 2/2001 | Asah | |
| 6,283,956 B1 | 9/2001 | McDaniel | |
| 6,302,874 B1 | 10/2001 | Zhang et al. | |
| 6,413,268 B1 | 7/2002 | Hartman | |
| 6,436,127 B1 | 8/2002 | Anderson | |
| 6,459,087 B1 | 10/2002 | Kaas | |
| 6,497,719 B2 | 12/2002 | Pearl et al. | |
| 6,524,330 B1 | 2/2003 | Khoobehi et al. | |
| 6,645,230 B2 | 11/2003 | Whitehurst | |
| 6,663,659 B2 | 12/2003 | McDaniel | |
| 6,676,655 B2 | 1/2004 | McDaniel | |
| 6,887,260 B1* | 5/2005 | McDaniel | 607/88 |
| 6,936,044 B2 | 8/2005 | McDaniel | |
| 7,004,933 B2 | 2/2006 | McDaniel | |
| 7,115,120 B2 | 10/2006 | Lin | |
| 7,201,765 B2* | 4/2007 | McDaniel | 607/88 |
| 2003/0004556 A1 | 1/2003 | McDaniel | |
| 2004/0215293 A1 | 10/2004 | Eells et al. | |

FOREIGN PATENT DOCUMENTS

| | | |
|---|---|---|
| EP | 0-298-661 | 1/1989 |
| GB | 2-262-043 | 6/1993 |
| GB | 2-360-461 | 9/2001 |
| JP | 07-016304 | 1/1995 |
| JP | 2000-202044 | 7/2000 |
| WO | WO-99/39763 | 8/1999 |
| WO | WO 00/02491 | 1/2000 |
| WO | WO 00/40266 A | 7/2000 |
| WO | WO 03/086215 | 10/2003 |
| WO | WO-2005/077452 A1 | 8/2005 |
| ZA | 97/07751 | 8/1997 |

OTHER PUBLICATIONS

"Laser Hair Care," Model 4000, 1996, www.laserhaircare.com/laserhair/background.html.

A. Doukas et al. (1996) "Physical Characteristics and Biological Effects of Laser-Induced Stress Waves," *Ultrasound in Med. & Biol.* 22(2), pp. 151-164.

A. Finlay et al. (1982) "A Fluorescence Photographic Photometric Technique to Assess Stratum Corneum Turnover Rate and Barrier Function Vivo," *British Journal of Dermatology* 107, pp. 35-42.

Abergel et al., (1987) "Biostimulation of Wound Healing by Lasers: Experimental Approaches in Animal Models and in Fibroblast Cultures" *J. Dermatol. Surg. Oncol.* 13(2), pp. 127-133.

Alain Rolland et al. (1993) "Site-Specific Drug Delivery to Pilosbaceous Structures Using Polymeric Microspheres," *Pharmaceutical Research* 10(12), pp. 1738-1744.

B. Krammer et al. (Feb. 1993) "Photodynamic Effects on the Nuclear Envelope of Human Skin Fibroblasts," *Journal of Photochem Photobiol. B: Biol.* 17(2), pp. 109-114.

Bommannan et al. (1992) "Sonophoresis I. The Use of High-Frequency Ultrasound to Enhance Transdermal Drug Delivery," *Pharmaceutical Research* 9(4), pp. 559-564.

Bommannan et al. (1992) "Sonophoresis II. Examination of the Mechanisms of Ultrasound-Enhanced Transdermal Drug Delivery," Pharmaceutical Research 9(8), pp. 1043-1047.

Brigette Illel et al. (1991) "Follicles Play an Important Role in Percutaneous Absorption," *Journal of Pharmaceutical Sciences* 80(5).

Burgess "Researchers Identify Key to Phototropism," *Biophotonics International*, Nov./Dec. 1999, pp. 22-23.

C. Green et al. (1988) "311 nm UVB Phototherapy: an Effective Treatment for Psoriasis," Br J Dermatol. 119, pp. 694-696.

Castro (Sep. 1983) "Effects of the Nd:YAG Laser on DNA SYnthesis and Collagen Production in Human Skin Fibroblast Cultures" *Annals of Plastic Surgery* 11, pp. 3.

Charlotte Phillips et al. (1992) "Ascorbic Acid and Transforming Growth Factor-B1 Increase Collagen Biosynthesis via Different Mechanisms: Coordinate Regulation of Proa1(I) and Proa1(III) Collagens," *Archives of Biochemistry and Biophysics* 295(2), pp. 397-403.

Charlotte Phillips et al. (1994) "Effects of Ascorbic Acid on Proliferation and Collagen Synthesis in Relation to the Donor Age of Human Dermal Fibroblasts," *The Journal of Investigative Dermatology* 103(2).

Chinese Office Action dated Oct. 14, 2005, directed to counterpart Chinese Application No. 028247698.

Chukuka S. Enwemeka (Dec. 1989) "The Effects of Therapeutic Ultrasound on Tendon Healing," *Am. J. Phys. Med. & Rehabil.* 68(6), pp. 283-287.

D. F. Webster et al. "The Role of Cavitation in the In Vitro Stimulation of Protein Synthesis in Human Fibroblasts by Ultrasound," *Ultrasound in Med & Biol.* 4, pp. 343-351.

D. F. Webster et al. (1980) "The Role of Ultrasound-Induced Cavitation in the 'In Vitro' Stimulation of Collagen Synthesis in Human Fibroblasts," *Ultrasonics*, pp. 33-37.

D. J. Castro et al. (Dec. 1987) "Biostimulative Effects of Nd: YAG Q-Switch Dye on Normal Human Fibroblast Cultures: Study of a New Chemosensitizing Agent for the Nd:YAG Laser," *Laryngoscope*, 97(12), pp. 1454-1459.

Dan Roden, MD (1997) "Electrophysiology, Pacing and Arrhythmia," *Clin Cardiol* 20, pp. 285-290.

David Draper et al. (1995) "Temperature Changes in Deep Muscles of Humans During Ice and Ultrasound Therapies: an In Vivo Study," *JOSPT* 12(3).

Des Travers, Australasian Post, Feb. 11, 1989.

Doan et al, (1999) "In Vivo Effects of Therapeutic Ultrasound on Cell Proliferation, Protein Synthesis, and Cytokine Production by Human Fibroblasts, Osteoblasts, and Monocytes" *J. Oral Maxillofac Surg.* 57, pp. 409-419.

Douglas Darr et al. (1993) "Ascorbic Acid and Collagen Synthesis: Rethinking a Role for Lipid Peroxidation," *Archives of Biochemistry and Biophysics* 307(2), pp. 331-335.

Edwards, (May 2001) "Keeping Up with the LEDs," *Photonics Spectra*.

Ethel Tur et al. (1991) "Percutaneous Penetration of Methyl Nicotinate at Three Anatomic Sites: Evidence for an Appendagael Contribution to Transport?" *Skin Pharmacol* 4, pp. 230-234.

European Search Report dated Sep. 16, 2005, directed to counterpart EP Application No. 02761449.4.

F. Heuber et al. (1994) "Percutaneous Absorption of Estradiol and Progesterone in Normal and Appendage-Free Skin of the Hairless Rat: Lack of Importance of Nutritional Blood Flow," *Skin Pharmacol* 7, pp. 245-256.

G. Kesave Reddy et al. (1998) "Laser Photostimulation of Collagen Production in Healing Rabbit Achilles Tendons," *Lasers in Surgery and Medicine* 22, pp. 281-287.

G. Morrone et al. (Jul. 1998) "In Vivo Experimental Research of Rabbit Condrocytes Biostimulation with Diode Laser Ga-Al-As: a Preliminary Study," *Artif Cells Blood Substit Immobil Biotechnol.* 26(4), pp. 437-439.

G. Nicolau et al. (1987) "Deposition of Viprostol (a Synthetic PGE2 Vasodilator) in the Skin Following Topical Administration to Laboratory Animals," *Xenobiotica* 17(9), pp. 1113-1120.

Giamundo, (May 2001) "A Little Enlightenment," *Photonics Spectra*.

Goldman, (Oct. 1999) "FotoFacial is a Pulsed Light Patient Pleaser" *Skin & Allergy News*.

Gopinathan K. Menon et al. (1991) "Ultrasound Localization of Calcium in Psoriatic and Normal Human Epidermis," *Arch Dermatol* 127.

Gopinathan K. Menon et al. (1994) "High-Frequency Sonophoresis: Permeation Pathways and Structural Basis for Enhanced Permeability," *Skin Pharmacol.* 7, pp. 130-139.

Gupta et al., (1998) "The Use of Low Energy Photon Therapy (LEPT) in Venous Leg Ulcers: A Double-Blind, Placebo-Controlled Study" *Dermatol. Surg.* 24, pp. 1383-1386.

Gupta et al. (1997) "The Use of Low-Energy Therapy In The Treatment of Leg Ulcers- A Preliminary STudy," *Journal of Dermatological Treatment* 8(2), pp. 103-108.

H. Van Weelden et al. (1990) "Comparison of Narrow band UV-B Phototherapy and PUVA Photochemotherapy in the Treatment of Psoriasis," Acta Dermatol Venereol (Stockh) 70, pp. 212-215.

Hans Schaefer et al. (1996) "Skin Barrier Principles of Percutaneous Absorption," pp. 153 and 175.

Heather A. Benson et al. (1991) "Influence of Ultrasound on the Percutaneous Absorption of Nicotinate Esters," *Pharmaceutical Research* 8(2), pp. 204-209.

Heather A. E. Benson et al. (1988) "Transmission of Ultrasound Energy Through Topical Pharmaceutical Products," *Physiotherapy* 74(11), pp. 587-589.

Huxiong Cheng et al. (1995) "Chemical Generation of Acoustic Waves: A Giant Photoacoustic Effect," *Science* 270.

J. Kao et al. (1988) "In Vitro Percutaneous Absorption in Mouse Skin: Influence of Skin Appendages," *Toxicology and Applied Pharmacology* 94, pp. 93-103.

J. Pospisilova et al. (1977) "Ultrasonic Effect on Collagen Synthesis and Deposition in Differently Localized Experiemental Granulomas," *Acta Chirurgiae Plasticae* 19, pp. 148-156.

James Ferry et al. (1990) "Relationship Between Contact Time of Applied Dose and Percutaneous Absorption of Minoxidil from a Topical Solution," Journal of Pharmaceutical Sciences 79(6).

Jean-Paul Ortonne (1989) "Psoralen Therapy in Vitiligo," *Clinics in Dermatology* 7(2).

John Murphy (1995) "From Submarines to Rehab: New Developments in Ultrasound," *Advance Rehabilitation*.

Joseph T. Newman et al. (Aug. 1992) "Hydrocortisone Phonophoresis, A Literature Review," *Journal of the American Podiatric Medical Association* 82(8), pp. 432-435.

Jui-Chen Tsai et al. (1992) "Drug and Vehicle Deposition from Topical Applications: Use of In Vitro Mass Balance Technique with Minoxidil Solutions," *Journal of Pharmaceutical Sciences* 81(8).

K. Gierlich et al. "Physikalische Medizin and Rehabilitation Heft Sep. 1968" The Combined Application of Ultrasound and Stimulation Currents, Reprint from the Journal.

Kamel Egbaria et al. (1992) "Adsorption of Fluorescein Dyes on Albumin Microspheres," *Pharmecutical Research* 9, pp. 629-635.

Katsuro Tachibana (1992) "Transdermal Delivery of Insulin to Allosxan-Diabetic Rabbits by Ultrasound Exposure," Pharmaceutical Research 9(7).

Katsuro Tachibana et al. (1993) "Use of Ultrasound to Enhance the Local Anesthetic Effect of Topically Applied Aqueous Lidocaine," *Anesthesiology* 78(6), pp. 1091-1096.

Kemmatp et al., (May 2001) "What Color is my LED?" *Photonics Spectra*.

Labbe et al., (1990) "Laser Photobioactivation Mechanisms: In Vitro Studies Using Ascorbic Acid Uptake and Hydroxyproline Formation as Biochemical Markers of Irradiation Response" *Lasers in Surgery and Medicine* 10, pp. 201-207.

Linda Lieb et al. (1992) "Topical Delivery Enhancement with Multiamellar Liposomes into Pilosebaceous Units: I. In Vitro Evaluation Using Fluorescent Techniques with the Hamster Ear Model," *The Journal of Investigative Dermatology* 99(1).

Lingna Li et al. (1992) "Product-Delivering Liposomes Specifically Target Hair Follicles in Histocultured Intact Skin," *In Vitro Cell Dev. Biol.* 28A, pp. 679-681.

Loevschall, (1994) "Effect of Low Level Diode Laser Irradiation of Human Oral Mucosa Fibroblasts in Vitro" *Lasers in Surgery and Medicine* 14, pp. 347-354.

Luther Kloth et al. (1996) "Promotion of Wound Healing with Electrical Stimulation," *The Journal for Prevention and Healing Advances* 9(5).

M. Dyson "The Effect of Ultrasound on the Rate of Wound Healing and the Quality of Scar Tissue," Department of Anatomy, Guy's Hospital Medical School, London, England pp. 110-122.

M. F. Coldman et al. (1969) "Enhancement of Percutaneous Adsorption by the Use of Volatile: Nonvolatile Systems as Vehicles," *Journal of Percutaneous Sciences* 58(9).

M. Hrnjak et al. (Nov. 1995) "Stimulatory Effect of Low-Power Density He-Ne Radiation on Human Fibroblast In Vitro," *Vojnosanit Pregl.* 52(6), pp. 539-546.

M. J. Callam et al. (Jul. 1987) "A Controlled Trial of Weekly Ultrasound Therapy in Chronic Leg Ulceration," *The Lancet*, pp. 204-206.

M. Pogrel et al. (1997) "Effects of Low-Energy Gallium-Aluminum-Arsenide Laser Irradiation on Cultured Fibroblasts and Keratincytes," *Lasers in Surgery and Medicine* 20, pp. 426-432.

M. Suzuki et al. (1978) "Autoradiographic Study on Percutaneous Absorption of Several Oils Useful for Cosmetics," *J. Soc. Cosmet. Chem.* 29, pp. 265-282.

Mary Dyson (Sep. 1982) "Stimulation of Tissue Repair by Therapeutic Ultrasound," *Infections in Surgery*.

Mary Dyson et al. (Apr. 1978) "Stimulation of Tissue Repair by Ultrasound: A Survey of the Mechanisms Involved," *Physiotherapy* 64(4), pp. 105-108.

McDaniel, (May 2001) "Nonablative Skin Rejuvenation-The Wave of Future" *Cosmetic Surgey Times*.

McDaniel, D. H. et al. (1996) "Treatment Of Stretch Marks With The 585 Nm Flashlamp-Pumped Pulsed Dye Laser," *Dermatological* 22(4), pp. 332-337.

Michelle Pronsati (Mar. 1992) "Uniformity Needed in Therapeutic Use of Ultrasound," *Advance for Physical Therapists*.

Miklos M. Breuer (Jun. 1998) "Ultrasonic Radiation for Hair Treatments," *Cosmetics & Toiletries* 113, pp. 67-75.

Montfrecola, G et al. (1987). "Topical Hematoporphyrin Plus UVA for Treatment of Alopecia Areata," *Photodermatology* 4:305-306.

N. Weiner et al. (1994) "Liposomes: A Novel Topical Delivery System for Pharmaceutical and Cosmetic Applications," *Journal of Drug Targeting* 2, pp. 405-410.

Nancy Gann (1991) "Ultrasound: Current Concepts," *Electrotherapy* 11(4).

Nancy N. Byl et al. (Jul. 1992) "Low-Dose Ultrasound Effects on Wound Healing: A Controlled Study with Yucatan Pigs," *Arch. Phys. Med. Rehabil.* 73, pp. 656-664.

P. Asawanonda et al. (May 2000) "308-nm Excimer Laser for the Treatment of Psoriasis," *Arch Dermtol.* 136, pp. 619-624.

P. Lehmann et al. (1991) "Effects of Ultraviolet A and B on the Skin Barrier: a Functional, Electron Microscopic and Lipid Biochemical Study," *Photodermatol Photoimmunol Photomed.* 8, pp. 129-134.

P. Morganti et al. (1997) "Enhancing the Glycolic Acid Efficacy by Piezolectric Vibrations," *J. Appl. Cosmotol.* vol. 15, pp. 147-159.

Parminder Singh et al. (1993) "Iontophoretic Transdermal Delivery of Salicylic Acid and Lidocaine to Local Subcutaneous Structures," *Journal of Pharmaceutical Sciences* 82(2).

Parrish et al. (1981). "Action Spectrum for Phototherapy of Psoriasis," *Journal of Investigative Dermatology* 76(5):359-362.

Patrick G. De Deyne et al. (Jul. 1995) "In Vitro Effects of Therapeutic Ultrasound on the Nucleus of Human Fibroblasts," *Physical Therapy* 75(7), pp. 629-634.

Polo, et al., (1999) "Role of Ground and Excited Singlet State Ozygen in the Red Light-Induced Stimulation of *Escherichia coli* Cell Growth" *Biochemical and Biophysical Research Communications* 257, pp. 753-758.

Pontinen et al. (1996) The Effect of Hair Lasers on Skin Blood Flow, Acupuncture & Electrotherapeutic Res. Int. J. vol. 21, pp. 105-118.

R. F. Lyons et al. (1987) "Biostimulation of Wound Healing in Vivo by a Helium-Neon Laser," *Ann Plast. Surg.* 18(1), pp. 47-50.

Richard Brucks et al. (1989) "The Effect of Ultrasound on the In Vitro Penetration of Ibuprofen Through Human Epidermis," Pharmaceutical Research 6(8), pp. 697-701.

Robert Scheuplein et al. (1971) "Permeability of the Skin," *Physiological Review* 51(4).

Ronald Wester et al. (1980) "Variations in Percutaneous Absorption of Testosterone in the Rhesus Monkey Due to Anatomic Site of Applications and Frequency of Application," Arch Dermatol Res. 267, pp. 229-235.

S. Borelli (1955) "Chlorophyll in the Treatment 1-27 of Acne Vulgaris," Dermatologie, Venerologie, und Verwandte Gebiete 6(7), pp. 320-324.

S. Mordon et al. (1997) "Selective Laser Photocoagulation of Blood Vessels in a Hamater Skin Flap Model Using a Specific ICG Formulation," *Lasers in Surg. & Med.* 21, pp. 365-373.

S. Mordon et al. (1997) "Thermal Damage Assessment of Blood Vessels in a Hamster Skin Flap Model by Fluorescence Measurement of a Liposome-Dye System," *Lasers in Surg & Med.* 20, pp. 131-141.

Samir Mitragotri et al. (1995) "A Mechanistic Study of Ultrasonically-Enhanced Transdermal Drug Delivery," *Journal of Pharmaceutical Sciences* 84(6), pp. 697-706.

Samir Mitragotri et al. (Aug. 1995) "Ultrasound-Mediated Transdermal Protein Delivery," *Science* 269, pp. 850-853.

Saran Kumar et al. (1992) "Studies of In Vitro Skin Permeation and Retention of a Leukotriene Antagonist from Topical Vehicles with a Hairless Guinea Pig Model," *Journal of Pharmaceutical Sciences* 81(7).

Schindl et al., (Sep. 2000) "Low-Intensity Laser Therapy: A Review" Journal of Investigative Medicine, 48(5).

Shalita et al., (2001) "Acne PhotoClearing (APC) Using a Novel, Hight-Intensity, Enhanced, Narrow-Band, Blue Light Source" *Clinical Application Notes* 9(1).

Sheldon Pinnell (1985) "Regulation of Collagen Biosynthesis of Ascorbic Acid: A Review,"The Yale Journal of Biology and Medicine 58, pp. 553-559.

Shingo Tajima et al. (1996) "Ascorbic Acid Preferentially Enhances Type I and III Collagen Gene Transcription in Human Skin Fibroblasts," *J. Dermatol Sci.* 11(3), pp. 250-253.

Skinner et al., (1996) "A Preliminary Study of the Effects of Laser Radiation on Collagen Metabolism in Cell Culture" *Australian Dental Journal* 41(3), pp. 188-192.

Sommer et al., (2001) "Biostimulatory Windows in Low-Intensity Laser Activation: Lasers, Scanners and NASA's Light Emitting Diode Array System" *Journal of Clinical Laser Medicine & Surgery* 19(1), pp. 29-33.

Sroka et al., (1999) "Effects on the Mitosis of Normal and Tumor Cells Induced by Light Treatment of Different Wavelengths" *Lasers in Surgery and Medicine* 25, pp. 263-271.

Stephen Guffey et al. (1991) "More than a Thermal Modality: Ultrasound," *Advance Rehabilitation*.

Sumian et al. A New Method to Improve Penetration Depth of Dyes into the Follicular Duct: Potential Application for Laser Hair Removal.

T. B. Melo (1987) "Uptake of Protoporphyrin and Violet Light Photodestruction of *Propionibacterium acnes*," *Journal of Biosciences* 42(1-2), pp. 123-128.

T. Omura (Nov. 1984) "Hemoprotein H-450 Identified as a Form of Cytochrome P-450 Having an Endogenous Ligand at the 6th Coordination Position of the Heme," *J. Biochem* 96(5), pp. 1491-1500.

The International Congress of Esthetics, Oct. 25-27, 1997, Convention Program.

Thomas Franz (Feb. 1985) "Percutaneous Absorption of Minoxidil in Man," *Arch Dermatol* 121.

V. Drastichova et al. (1973) "Strengthening of Sutured Skin Wound with Ultrasound in Experiments on Animals," *Acta Chirurgiae Plasticae* 15, pp. 114-119.

V. Srinivasan et al. (1989) "Transdermal Iontophoretic Drug Delivery: Mechanistic Analysis and Application to Polypeptide Delivery," *Journal of Pharmaceutical Sciences* 78(5).

V. Srinivasan et al. (1990) "Ionotphoresis of Polypeptides: Effect of Ethanol Pretreatment of Human Skin," *Journal of Pharmaceutical Sciences* 79(7).

Van Breugel et al. (1992) "Power Density and Exposure Time of He-Ne Laser Irradiation are More Important Than Total Energy Dose in Photo-Biomodulation of Human Fibroblasts in Vitro" *Lasers in Surgery and Medicine* 12, pp. 528-537.

Vreman et al., (1998) "Light-Emitting Diodes: A Novel Light Source for Phototherapy" 44, pp. 5.

W. Harvey et al. (1975) "The Stimulation of Protein Synthesis in Human Fibroblasts by Therapeutic Ultrasound," *Rheumatology and Rehabilitation* 14, 237.

W. Westerhof et al. (1997) "Treatment of Vitiligo with UV-B Radiation vs. Topical Psoralen Plus UV-A," *Arch. Dermatol.* 133, pp. 1525-1528.

W. Yu et al. (1997) "Effects of Photostimulation on Wound Healing in Diabetic Mice," *Lasers Sug. Med.* 20(1), pp. 56-63.

Webb, et al., (1998) "Stimulatory Effect of 660 nm Low Level Laser Energy on Hypertrophic Scar-derived Fibroblasts: Possible Mechanisms for Increase in Cell Counts" *Lasers in Surgery and Medicine* 22, pp. 294-301.

Wei Yu et al. (1997) "Improvement of Host Response to Sepsis by Photobiomodulation" *Lasers in Surgery and Medicine* 21, pp. 262-268.

Wolfgang Ritschel et al. (1989) "Percutaneous Absorption of Coumarin, Griseofulvin and Propanolol Across Human Scalp and Abdominal Skin," *Meth and Find Exp Clin Pharmacol.* 11(10), pp. 643-646.

Z. Joachims et al. (1987) "Noise-Induced Hearing Loss in Humans as a Function of Serum Mg Concentration," *Mag-Bull*, pp. 130-131.

Zelickson et al. (1999) "Pulsed Dye Laser Therapy for Sun Damaged Skin," *Lasers in Surgery and Medicine* 25, pp. 229-236.

"Chlorophyll," from Wikipedia located at <http://de.wikipedia.org/wiki/Chlorophyll, visited on Jul. 18, 2007. (5 pages).

"Porphin," from Wikipedia located at <en.wikipedia.org/wiki/Porphine, visited on Jul. 18, 2007. (2 pages).

European Written Opinion dated Jul. 31, 2007, directed to counterpart EP Application No. 02761449.4.

International Search Report and Written Opinion mailed May 22, 2008, directed to counterpart international application No. PCT/US2007/02958; 10 pages.

\* cited by examiner

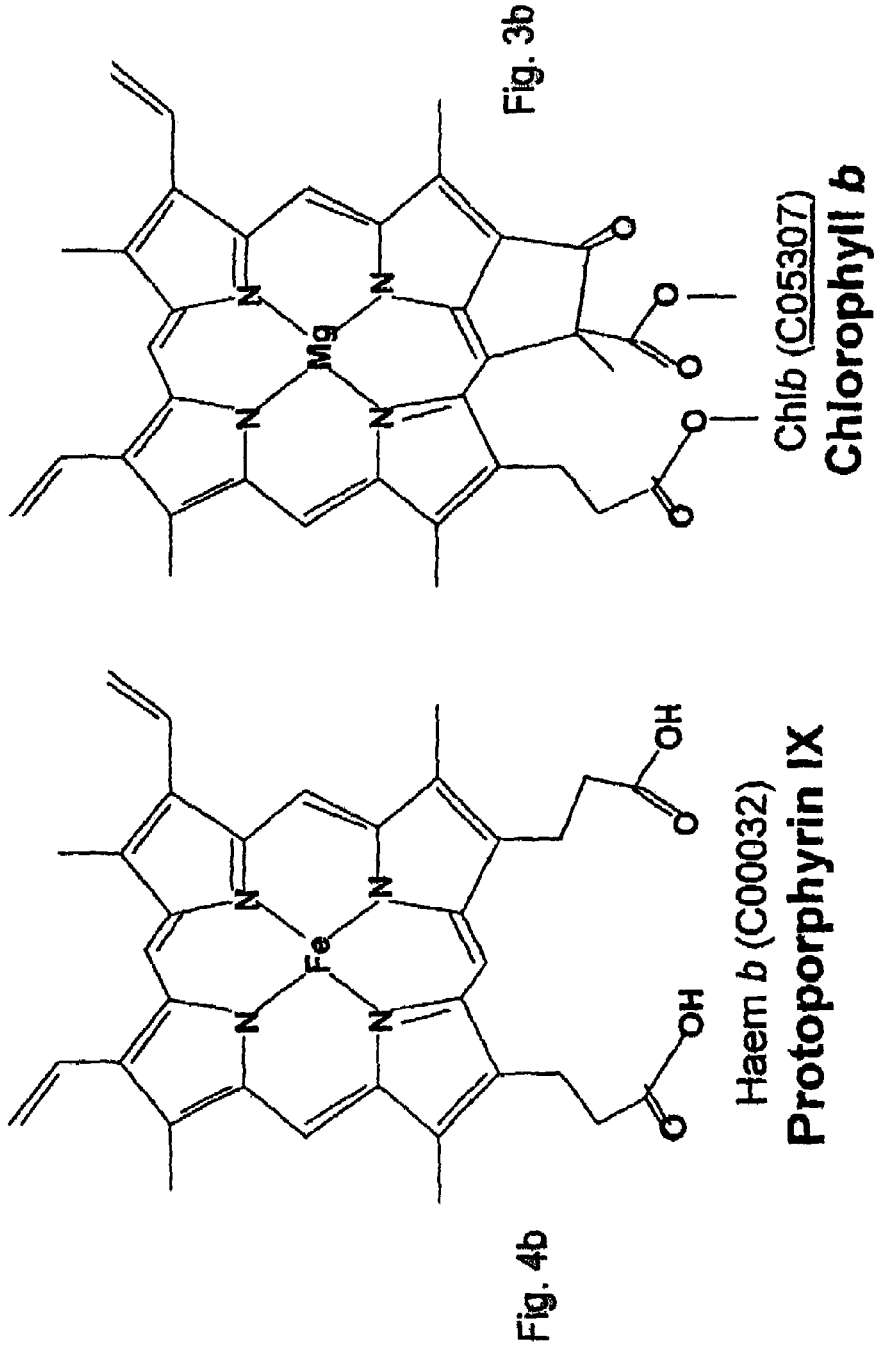

Pentacoordinate

Chlorophyll a

Pentacoordinate / Hexacoordinate

Protoporphyrin IX

LED ARRAY    SINGLE LED

METHOD AND APPARATUS FOR ACNE PREVENTION

This application is a continuation of Ser. No. 11/119,378, now U.S. Pat. No. 7,201,765 issued Apr. 10, 2007, which is a divisional of U.S. application Ser. No. 09/933,870 filed Aug. 22, 2001, now U.S. Pat. No. 6,887,260, which is a continuation-in-part of Ser. No. 09/819,082 filed Feb. 15, 2001, now abandoned, which is a divisional of Ser. No. 09/203,178, filed Nov. 30, 1998, now U.S. Pat. No. 6,283,956.

FIELD OF THE INVENTION

The present invention generally relates to a system and method for the prevention of sebaceous gland disorders and, more specifically, to the prevention of acne using a novel combination of photothermal, photochemical and photomodulatory means by applying a cosmeceutical composition, naturally occurring chromophore, or other light-activated chromophore to or into the oil gland and surrounding tissue and exposing the composition to electromagnetic radiation.

BACKGROUND OF THE INVENTION

There are several known techniques for attempting to reduce or eliminate the skin disorders associated with the activity of sebaceous oil glands. The primary disorder is acne with an associated disorder of acne scarring. A few of these known techniques are scientifically proven and widely accepted as effective. However, their degree of efficacy varies greatly.

There are several processes which may be used for inhibiting the activity of sebaceous oil glands. In one process the target may be duct of the gland and the treatment focuses on the treatment of sebaceous follicles to eliminate the associated disorders. In U.S. Pat. No. 6,183,773, to Anderson, which is hereby incorporated by reference, an attempt is made to treat sebaceous gland disorders using lasers which irradiate energy activatable material, primarily laser sensitive dyes, that have been applied to the skin.

Anderson teaches a method for treating skin disorders associated with sebaceous follicles by topically applying an energy activatable material to a section of skin afflicted with a sebaceous gland disorder, wherein the material is activated by energy which penetrates outer layers of epidermis. A sufficient amount of the material infiltrates the afflicted section of skin and is exposed to sufficient energy to cause the material to become photochemically or photothermally activated, thereby treating the sebaceous gland disorder. In one embodiment, the sebaceous gland disorder is acne. Suitable energy sources for use in accordance with Anderson's invention include flash lamp based sources and lasers, such as Nd:YAG, Alexandrite, flash lamp-pumped dyes and diodes. The energy source can be a continuous wave energy source or pulsed. In the preferred embodiment, the energy activatable material is a laser sensitive chromophore, e.g., a chromophore which is capable of being photoactived by a laser, e.g., a dye. Anderson describes a particularly preferred embodiment, wherein the chromophore is methylene blue.

Anderson's method, however, fails to take advantage of the recent developments in light emitting diode technology that permits the use of LEDs for dermatological use in place of much more expensive lasers. Further, due to the high-intensity nature of lasers, severe skin damage or other injury can occur when the light source is improperly operated. Further, the laser dyes and other topical compositions described by Anderson are expensive and require FDA approval for their intended use, making the invention expensive and time consuming to implement. Further, because of Anderson's focus on the oil gland itself, rather than the elimination of the acne bacteria, suitable results may not be achieved in all cases.

In WO 00/02491, to Harth et al., a method and apparatus are disclosed for eliminating acne bacteria through photothermal means by exposing the bacteria to a narrow band light source in the range of 405 nm to 440 nm. Harth et al., as well, failed to appreciate the opportunity for current LED technology to be applied to dermatologic treatment and, like Anderson, do not disclose means for treating sebaceous oil gland disorders without the high cost and time commitment necessary to receive FDA approval require for high-intensity light therapies with topical compositions such as methylene blue.

In each of the known attempts to treat sebaceous gland disorders, extensive investment in expensive light sources and topical drug composition testing is required. Moreover, none of these attempts addresses the secondary disorder associated with acne—acne scarring.

Consequently, it would be desirable to prevent and treat sebaceous gland disorders and, in particular, acne in a way that addresses, prevents and treats acne scarring without the need for expensive, potentially dangerous high-intensity light sources. Further, it would be beneficial for such a prevention or treatment regiment to include the use of naturally occurring compositions that fall into the category of cosmetics and cosmeceuticals that are generally recognized as safe and that do not require FDA approval, thereby eliminating the time and resource expenditures associated with the commercial implementation of such a prevention or treatment regime.

SUMMARY OF THE INVENTION

In one embodiment of the invention, the process for preventing skin disorders, and particularly the treatment of sebaceous oil glands comprises applying a photomodulation enhancing agent, such as a naturally occurring native chromophore, to the skin proximate to or directly to a sebaceous oil gland, tissue feeding said sebaceous oil gland, or both, and exposing said photomodulating enhancing agent to a source of electromagnetic radiation comprising at least one dominant emissive wavelength. The photomodulation enhancing agent should have an absorption characteristic at the dominant emissive wavelength carefully selected to cause the inhibition of, reduction in size of, or the destruction of sebaceous oil glands, tissue feeding off the sebaceous oil gland, or both.

Further, source of electromagnetic radiation may be selected from the ultrasound radiation, light emitting diodes, lasers such as laser diodes and dye lasers, metal halide lamps, flashlamps, mechanically filtered fluorescent light sources, mechanically filtered incandescent light sources, natural or filtered sunlight, or combinations thereof. In a preferred embodiment, the source of the electromagnetic radiation is a light emitting diode having a dominant emissive wavelength of from about 300 nm to about 1400 nm. Even more preferred is when the light emitting diode has a dominant emissive wavelength at one of 400 nm, 420 nm, 430 nm, 445 nm, 635 nm, 655 nm, 660 nm, 670 nm, 780 nm, 785 nm, 810 nm, 830 nm, 840 nm, 860 nm, 904 nm, 915 nm, 980 nm, 1015 nm, and 1060 nm.

In another preferred embodiment, the photomodulation enhancing agent has a local electromagnetic absorption maximum at the dominant emissive wavelength of the light source used for treatment. Further, prevention contemplated using the photomodulating enhancing agent requires exposing the agent to a plurality of pulses from said source of electromagnetic radiation for a therapeutically effective pulse length and pulse duration. In one embodiment of the invention, the exposure is to an LED emitter outputting about 2 milliwatts for about 20 minutes or to 100 milliwatts/cm$^2$ for 10 minutes from a metal halide light source, and in alternate embodiments, the electromagnetic radiation is emitted at an energy level of from about 0.1 W/cm$^2$ to about 5.0 W/cm$^2$.

The topical agent of the present invention may include particles of a size enabling penetration of a sebaceous oil gland duct. In particular, particles may have an average diameter of less than about 5 µm. More generally, the photomodulation enhancing agent is a composition made up of at least one of Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, epigallocatechin 3-gallate, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, carotenoids, bacteriochlorophyll, phycobilins, carotene, xanthophyll, anthocyanin, and derivatives and analogs of the above, both natural and synthetic, and mixtures thereof. The composition may be chlorophyll, carotenoids, derivatives thereof, and mixtures thereof.

The method of the present invention may be further enhanced by subjecting the photomodulation or photothermal enhancing agent to a penetration enhancing procedure prior to exposing the enhancing agent to the source of electromagnetic radiation. Such procedures increase permeability of the skin or decrease skin barrier function and may be helpful for optimizing the present invention. Options for this include, but are not limited to, stripping, removing, thinning or diminishing the structure, function, thickness or permeability of the stratum corneum by various mechanical, abrasive, photo acoustical, ablative, thermal, chemical, abrasive or enzymatic methods. Examples of these could include solvent or tape stripping, scrubbing, laser ablation or vaporization, chemical peeling, micro dermabrasion, enzyme peeling, or laser treatment using high peak power, short pulse duration lasers.

The method of the present invention may be carried out with a light source alone or, preferably, in combination with one of the topical compositions listed above. In either case, a preferred source of electromagnetic radiation is a light emitting diode having a dominant wavelength of 410 nm and a bandwidth of +/−at least 5 nm. Further, use of various light sources to enhance the treatment of the present invention by photothermal means is also desirable for some forms of treatment. The present invention may be used as described or in conjunction with traditional acne skin care treatments and kits.

BRIEF DESCRIPTION OF THE DRAWINGS

FIG. 3*b* shows the structure of chlorophyll b.

FIG. 10 shows the absorption spectrum for human fibroblast overlaid with the wavelengths of various, commercially produced LEDs, and also the absorption spectrum of chlorophyll a.

Figure 1:
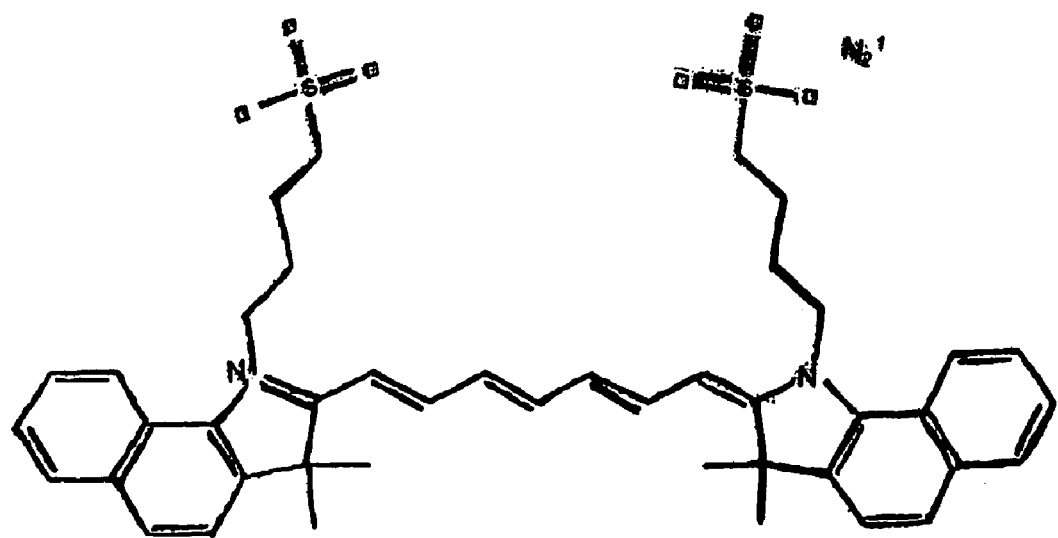
FIG. 1 is an illustration of the chemical structure of methylene blue.

A detailed description of a preferred embodiment of the present invention will be made with reference to the accompanying drawings.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, the present invention is directed to a process for dermatologic treatment and prevention. Such prevention may include the photomodulation of sebaceous oil glands and the surrounding tissue or producing temporary or permanent reduction of activity or destruction of sebaceous oil glands or supporting tissue or the removal, in human or mammalian skin, of some or all of the hairs growing approximate to oil glands. In a preferred embodiment the process produces little or no permanent injury or damage to nearby skin tissue. Substantially only the oil gland and immediately surrounding tissue are affected.

In a process according to one embodiment of the present invention, an agent may be selected which is capable of penetrating the oil gland and surrounding tissue. The agent may be characterized as an active agent in that it performs a function in addition to simply occupying or contaminating the space in the ducts surrounding the gland. Alternatively, the agent may perform the passive function filling the void space in the ducts surrounding the glands, depending on the nature of the treatment desired. The agent may have sufficient optical absorption of a wavelength (or a combination of wavelengths) of a coherent or non-coherent light source which can penetrate the skin adequately to be absorbed by the target agent or the new agent-tissue complex.

The area of skin overlying where the oil gland is located may be cleansed. After the skin is cleansed, the skin may be treated to improve permeability. This may be accomplished, for example, by treating the skin with steam or a hot moist towel to hydrate the skin and hair or removing a portion of the stratum corneum through various means known in the art, exemplary of which is microdermabrasion.

The agent may be applied in sufficient quantity and in suitable form to be incorporated into the target tissue in adequate or optimal amounts to allow the production of the desired tissue effect.

Excess agent may be removed, neutralized, inactivated, decolorized, diluted or otherwise altered so that residual contamination of the skin by such excess agent is either (a) absent and does not interact with the light or energy source, or (b) present in such small quantity that it provides no clinical effect.

Delivery of the desired agent into the target tissues may be enhanced, facilitated or made possible by the use of enzymes capable of altering the structure, permeability, or other physical characteristics of the stratum corneum or by the use of ultrasound or phonophoresis either for penetration into the gland or surrounding target tissues or, once penetrated, to cause the release of the agent from the encapsulated delivery device such as liposomes, polymers, microspheres, etc. so as to cause penetration or attachment of this active agent. Ultrasound may be used therapeutically to interact directly with the agent or the agent-tissue complex to produce the desired damaged target tissues (to be used alone or in combination with laser or non-laser light sources). Microderm abrasion may also be used to permit greater penetration of the skin, wherein the upper epithelial layers are removed. These layers create a natural barrier to the permeability of the skin and, by their removal, penetration of the skin by topical agents is facilitated. This method may be further enhanced by using ultrasound, alone or in combination with alteration of the stratum corneum, to further improve the performance of topical compositions. A more detailed description of several aspects of the use of ultrasound may be found, for example, in the applicant's U.S. Pat. No. 6,030,374 for "Ultrasound Enhancement of Percutaneous Drug Absorption" which is hereby incorporated by reference in its entirety.

Although preferred embodiments of the present invention may use LEDs, ultrasound and/or laser or light energy, the present invention is not limited to the use of these energy sources. Other sources of energy, including (without limitation) microwave energy and radio frequency energy may also be used. Exemplary of known light sources are fluorescent lights, flashlamps, filamentous lights, etc. One skilled in the art will recognize that any light source capable of emitting electromagnetic radiation at a medically useful wavelength, as described herein, directly, or by means of optical filtration, is within the scope of suitable light sources according to the present invention. For purposes of the photomodulatory and photothermal treatment methods described, any source capable of emitting light having a wavelength from about 300 nm to about 1400 nm, or producing electromagnetic radiation which is filtered or otherwise altered to exposure the skin, a topical composition, or other component of the present treatment regime to a wavelength of light in the aforementioned range is medically useful.

Figure 14:
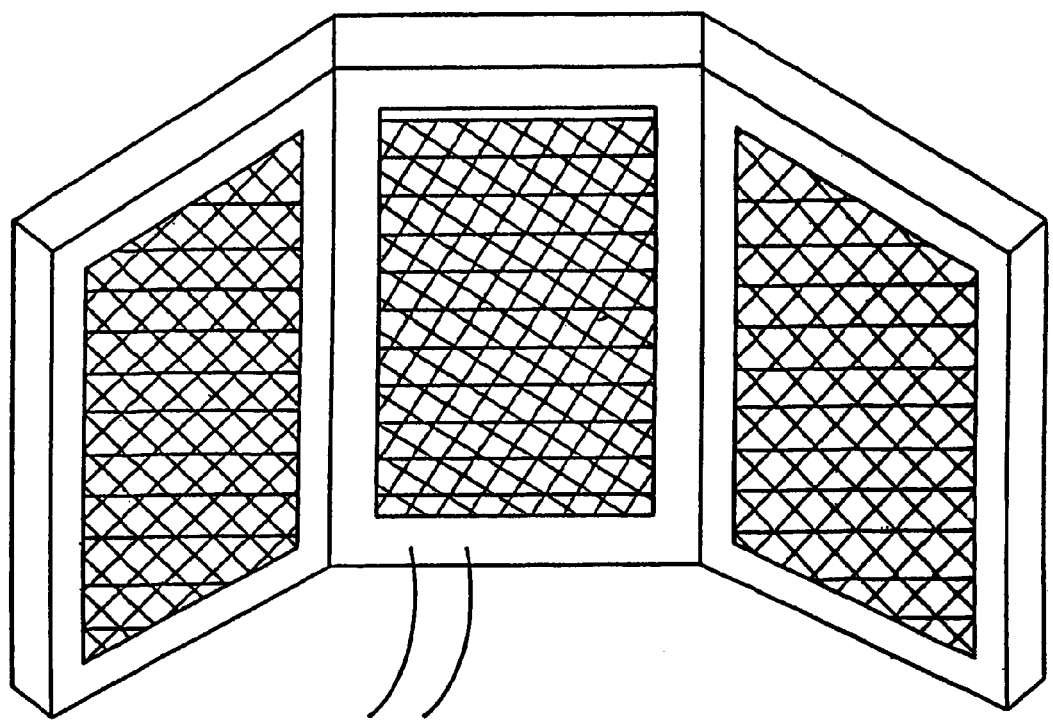
FIG. 14 depicts a front view, in perspective, of a three-panel array of LEDs for treatment in accordance with an embodiment of the present invention.
Figure 15:
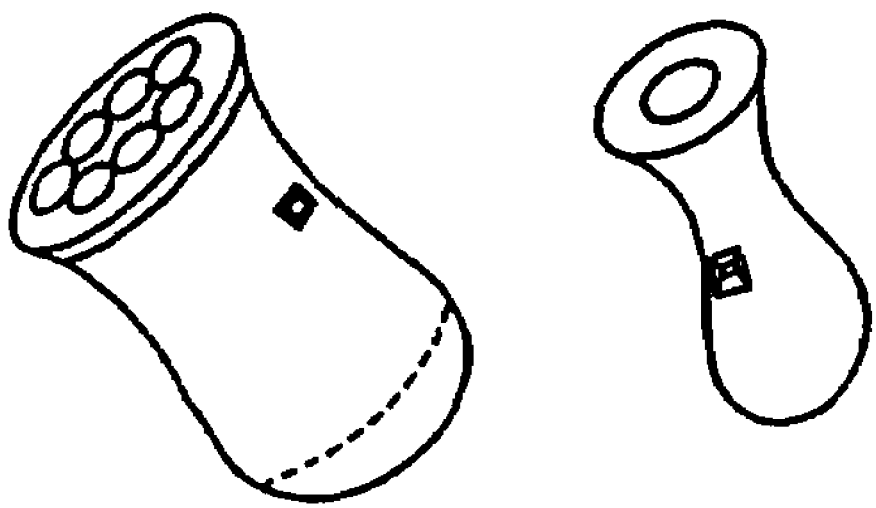
FIG. 15 is a perspective view of hand-held LED devices for treatment in accordance with the present invention.

The targeted skin may be exposed to one or more wavelengths of LED, laser or non-laser light such as filtered filamentous sources or fluorescent sources or single or multiple frequencies of ultrasound. A variety of parameters may be used (including pulse duration, energy, single or multiple pulses, the interval between pulses, the total number of pulses, etc.) to deliver sufficient cumulative energy to interact with the agent or tissue complex. This results in the inhibition or destruction of the sebaceous oil gland or the supporting skin tissue through photomodulatory means, photothermal means, or combinations thereof. Ultrasound may also be used to preheat the target structures or the entire skin. Further for treatment over a broad area of human skin, the light source may be diffused through a device such as a holographic diffuser; or, alternatively, the light source may be comprised of an array of individual emitters such as the three-panel array of LEDs illustrated in FIG. 14. For localized treatment, smaller arrays or individual LEDs, such as in the hand held devices depicted in FIG. 15 may be used. Since LED sources are considered "insignificant risk devices", no medical supervision is required and these devices may be used by the patient for at-home treatment or as part of an ongoing skin-care system after receiving treatment by a physician.

The topical agent may be incorporated into the target tissue by a variety of mechanisms. These mechanisms include, but are not limited to: 1) physical incorporation into the gland or target tissue cells while leaving the chemical structure essentially unaffected, or 2) undergoing a chemical reaction resulting in a new agent-tissue complex which then becomes a target for energy absorption.

The process may be a single or multi-step process and may involve the use of cofactors, catalysts, enzymes, or multiple agents which interact to ultimately become or create an active agent or agent-tissue complex.

Agents may include, without limitation, the following compositions and derivatives and analogs thereof: hair dyes, vegetable dyes, food coloring, fabric dyes, tissue stains, shoe or leather dyes, other plant products (such as flavonols, chlorophyll, copper chlorophyllin, bacteria chlorophylls, carotenoids, enzymes, monoclonal antibodies, any immunological agent, genetically engineered agent, benign infectious agents, whether naturally occurring or genetically engineered (e.g. the bacteria that normally reside on the skin such as acne bacteria, etc.), antibiotics, agents which attach to sebocytes in the sebaceous gland or duct cells directly, whether by topical or systemic agents that localize in these target tissues, including antibodies or antibody-chromophore compounds of these structures. The preceding list is illustrative and not exhaustive of those agents suitable for use in accordance with the present invention. In general, the topical agent chosen will have certain absorption characteristics that augment the penetration of the radiation to the tissue targeted for treatment, i.e., sebaceous oil gland, acne-scarred tissue, etc.

Figure 2:
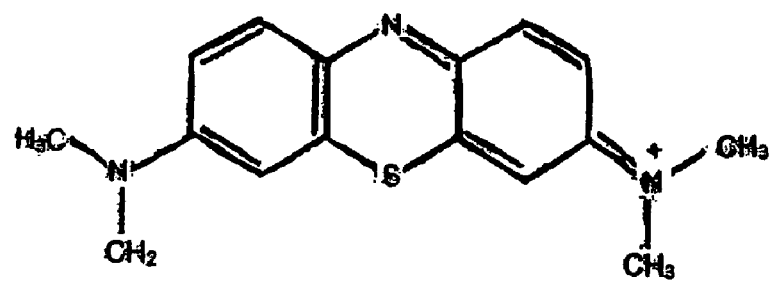
FIG. 2 shows the chemical structure of indocyanine green.
Figure 3A:
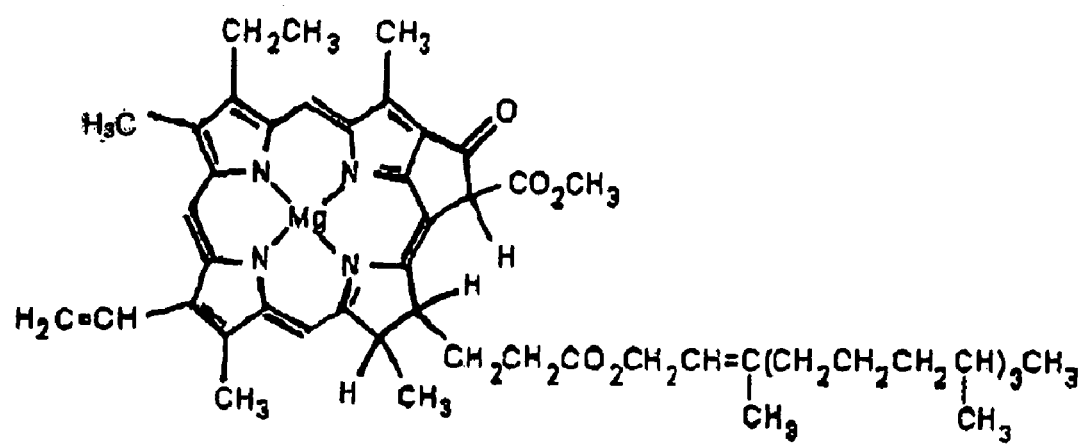
FIG. 3*a* is a representation of the general chemical structure of a chlorophyll molecule.
Figure 4A:
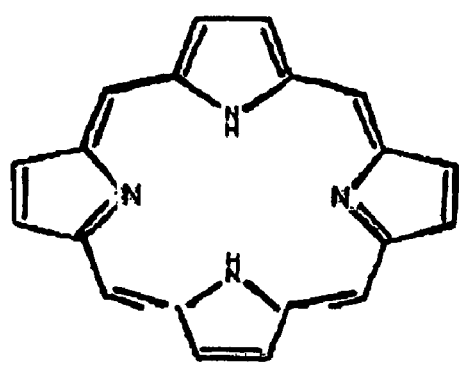
FIG. 4 shows the general chemical structure of a porphyrin molecule.
FIG. 4*b* shows the structure of porphyrin IX.
Figure 5A:
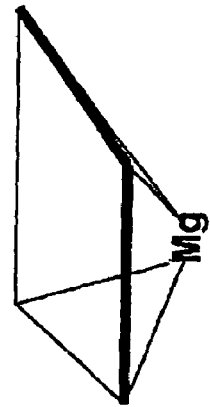
FIG. 5*a* illustrates the physical structure of the ligand bond portion of a chlorophyll a molecule.
Figure 5B:
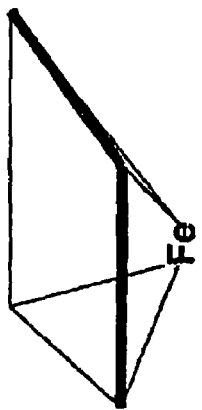
FIG. 5*b* illustrates the physical structure of the ligand bond portion of a protoporphyrin IX molecule.
Figure 6:
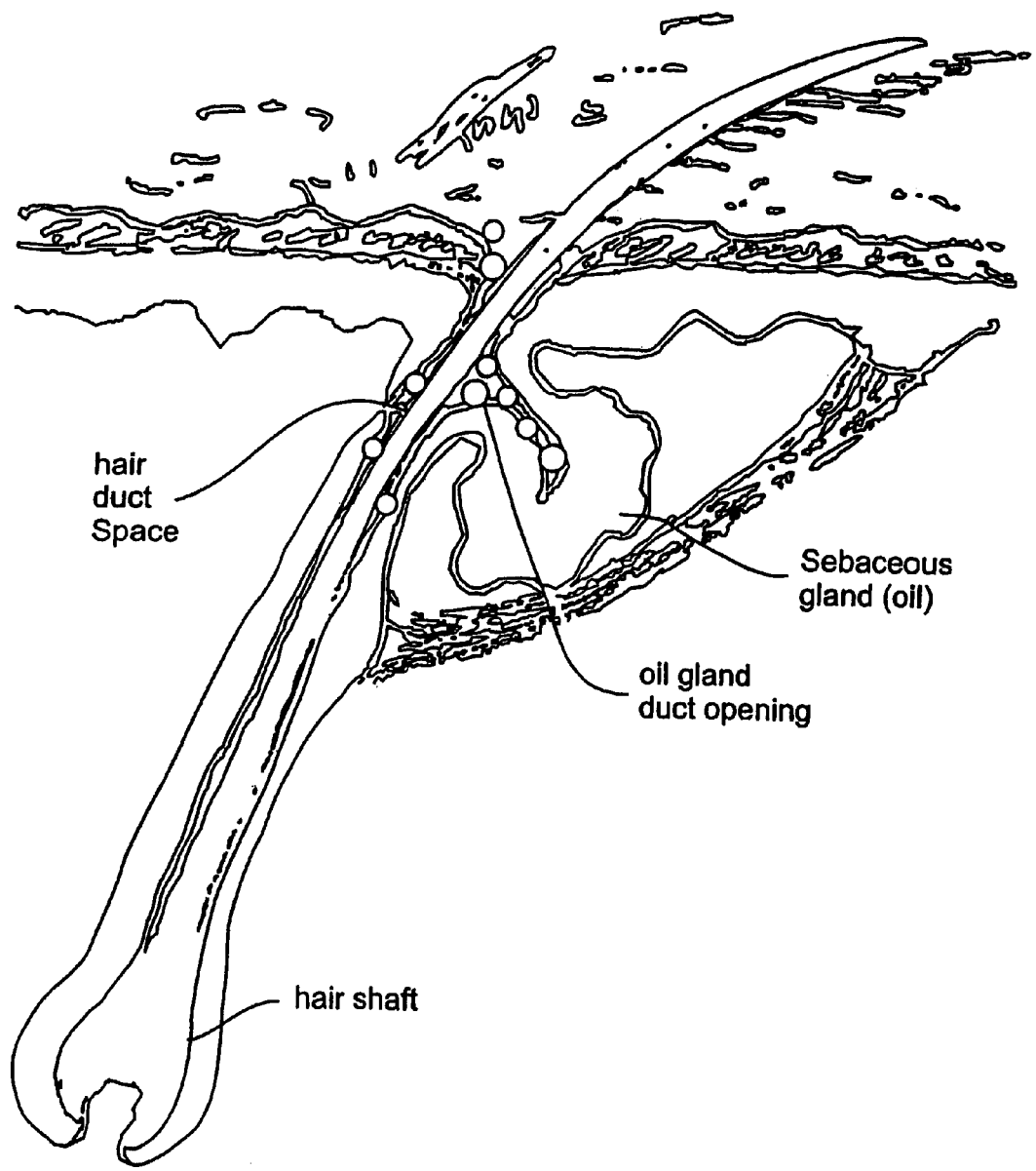
FIG. 6 illustrates a sweat gland and the epithelial layers of human skin.

Most preferable are topical compositions that include a quantity of a naturally occurring chromophore such as chlorophyll, chlorophyllin, polyporphyin, bacteriochlorophyll, protopolyporphyin, etc. These compositions are characterized by a metal-ligand bond as is illustrated in FIGS. 3*b* and 4*b*, specifically, and in FIGS. 3 and 4 more generally. Further, FIGS. 5*a* and 5*b* show the metal-ligand bond physical structure that is common to the naturally occurring native chromophores of the present invention, as well as the cyclic tetrapyrrole ring that chlorophyll shares with suitable cytochromes. In contrast, synthetic chromophores do not include a metal-ligand bond, nor do they exhibit the same general physical structure as naturally occurring chromophores, as is illustrated by the structure of methylene blue, FIG. 1, and indocyanine green, FIG. 2.

Agents may be delivered in pure form, in solution, in suspension, in emulsions, in liposomes, in synthetic or natural microspheres, microsponges or other known microencapsulation vehicles, alone or in combination. This list of the forms of the agents is illustrative and not exhaustive. Those skilled in the art will recognize that there are a wide variety of forms for the delivery of topical compositions suitable for use in accordance with this invention.

The process may include an application of an active agent and treatment with an energy source as a single treatment. Alternatively, treatment with an energy source may be delayed for hours or days after application of an active agent. Application of an active agent may be performed or applied at another location, such as patient's home, prior to the energy treatment.

After an energy treatment has occurred it may be desirable in some situations to remove, neutralize, decolorize or otherwise inactivate any residual active agent. In other situations, continued application to replenish depleted chromophore may be desirable.

Figure 7:
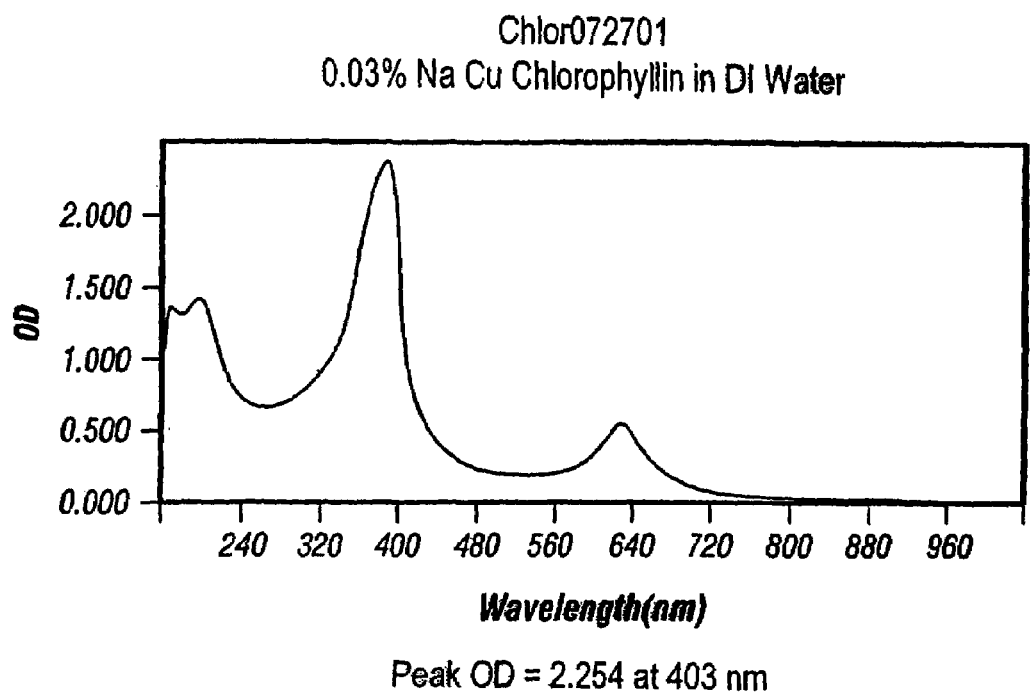
FIG. 7 is a graph showing the absorption spectrum of 0.03% Na Cu chlorophyllin in water.
Figure 8:
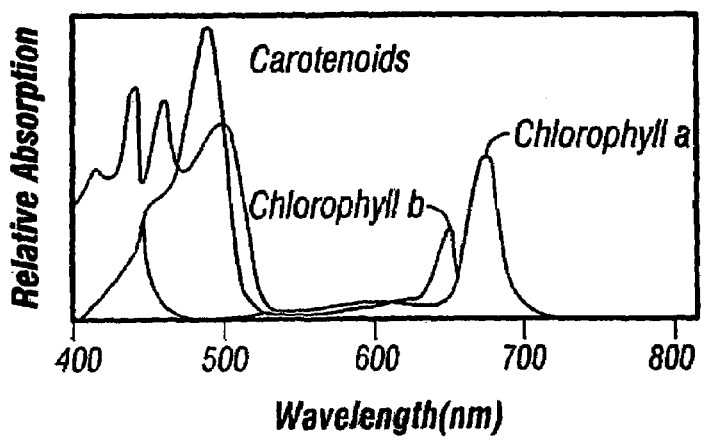
FIG. 8 illustrates the relative absorption spectra of various naturally occurring chromophores.
Figure 9:
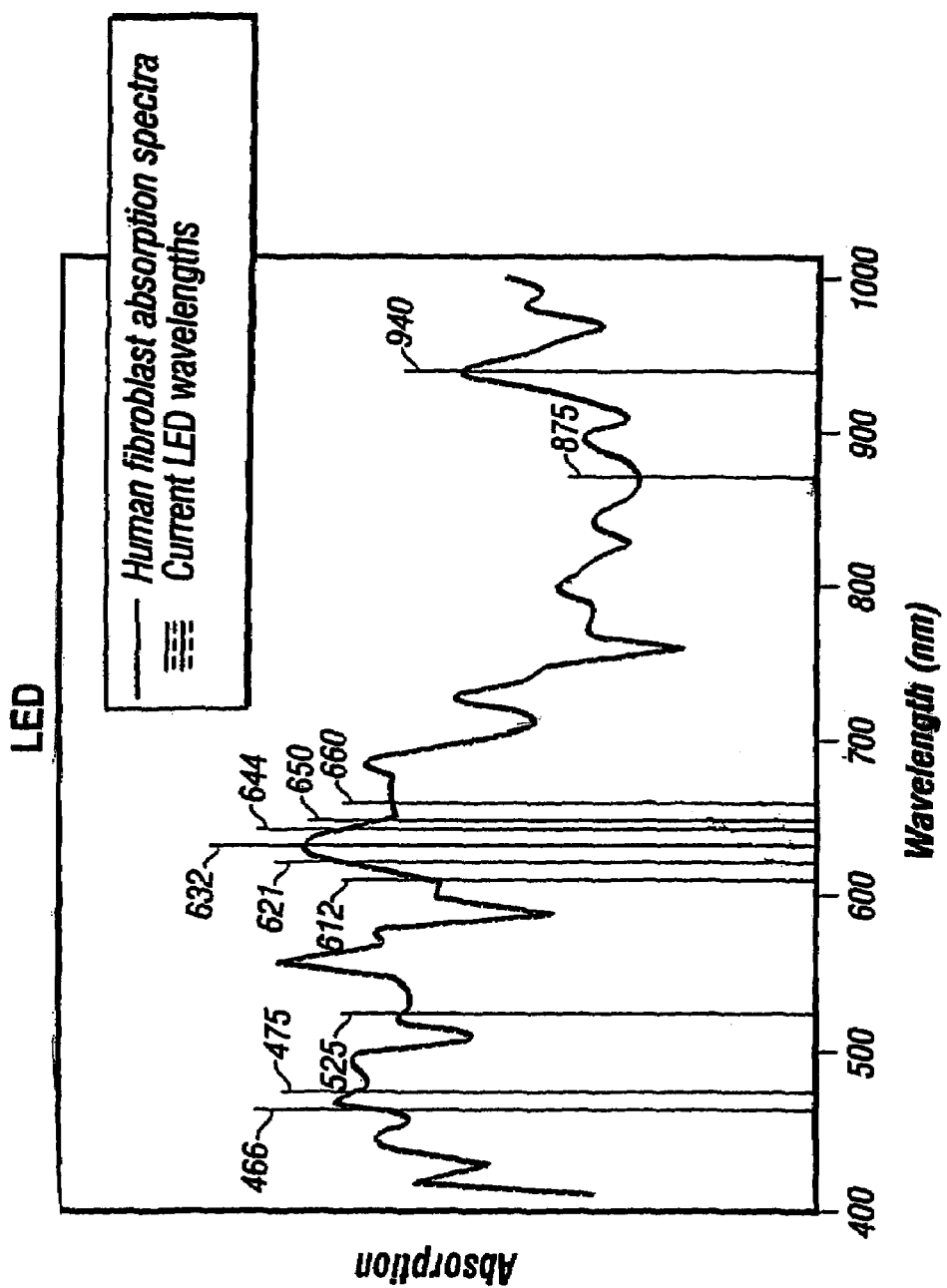
FIG. 9 shows the absorption spectrum for human fibroblast overlaid with the wavelengths of various, commercially produced LEDs.
Figure 10:
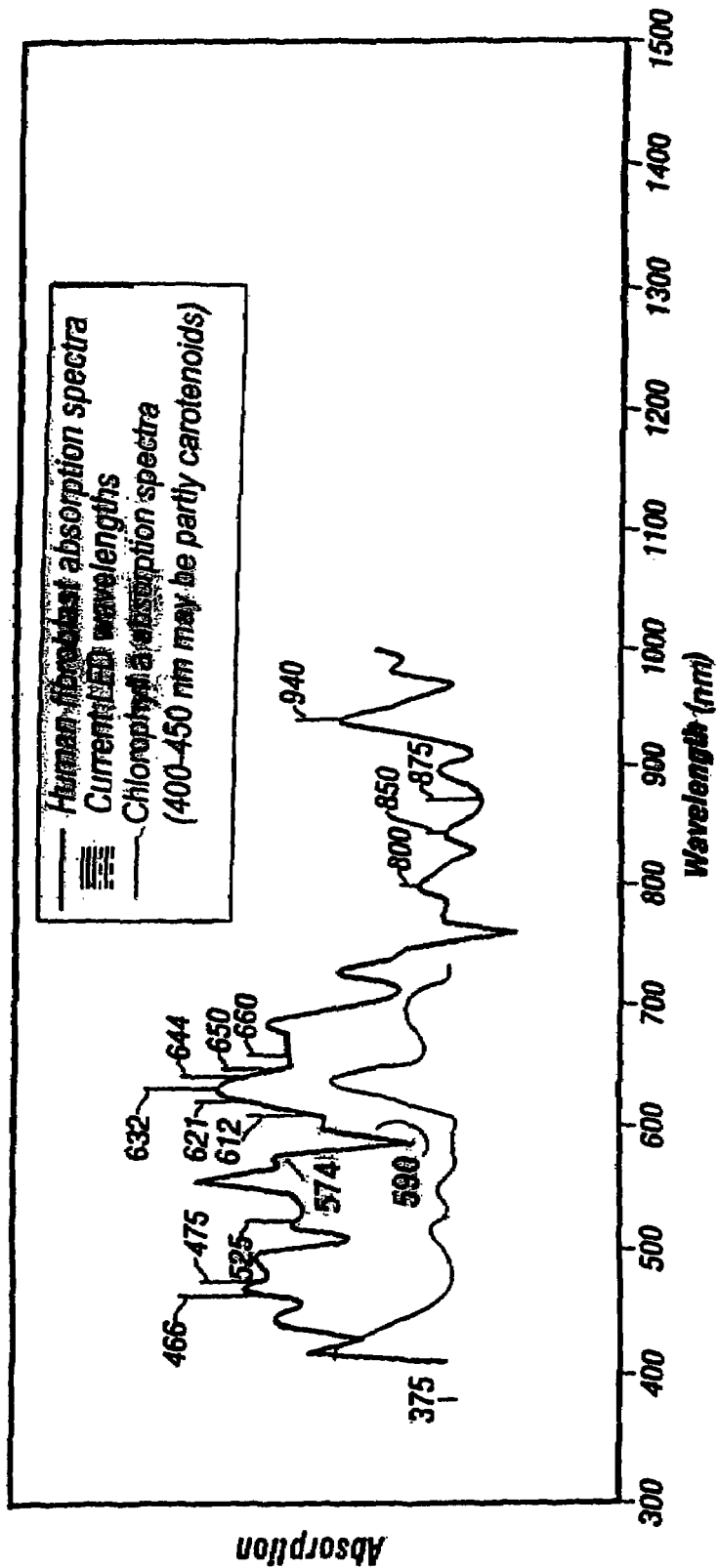
Figure 11:
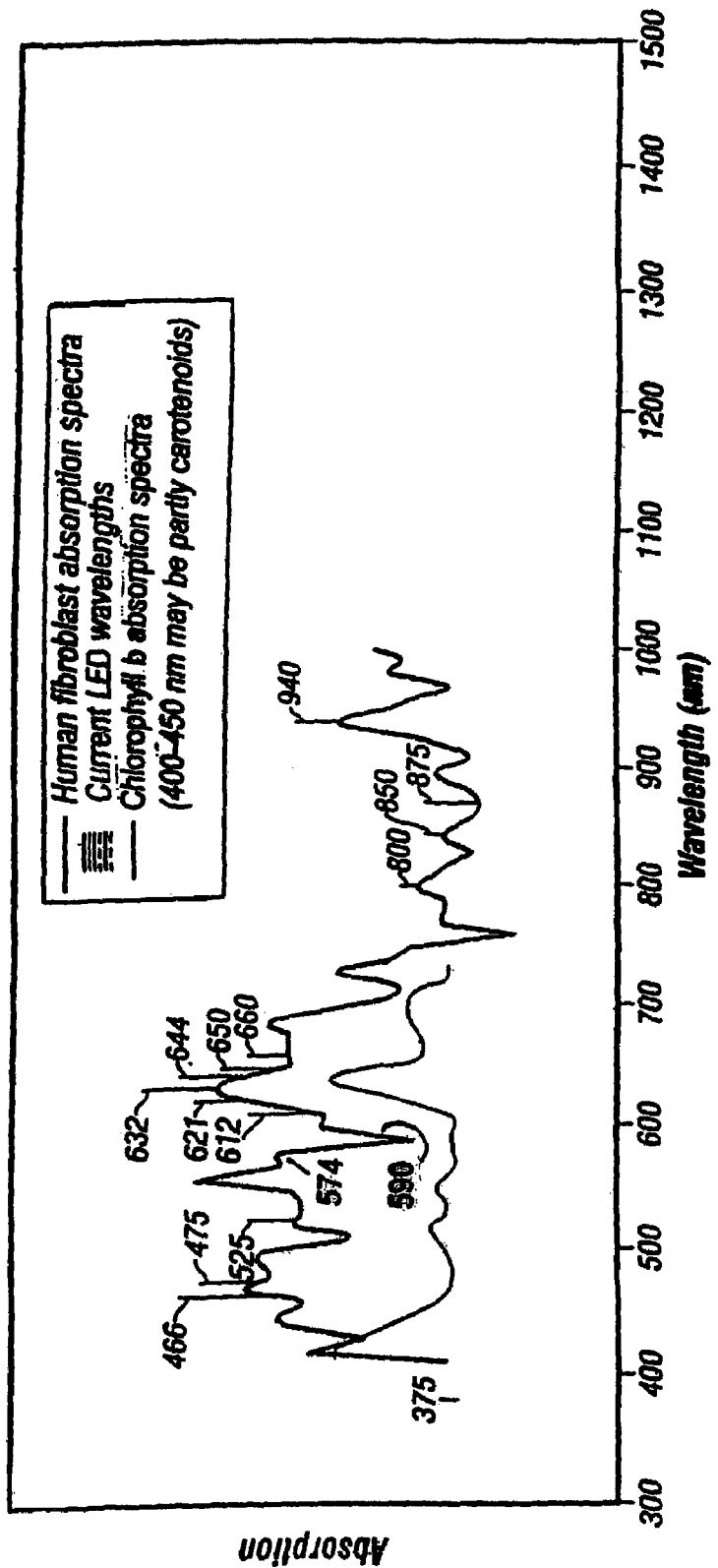
FIG. 11 shows the absorption spectrum for human fibroblast overlaid with the wavelengths of various, commercially produced LEDs, and also the absorption spectrum of chlorophyll b.
Figure 12:
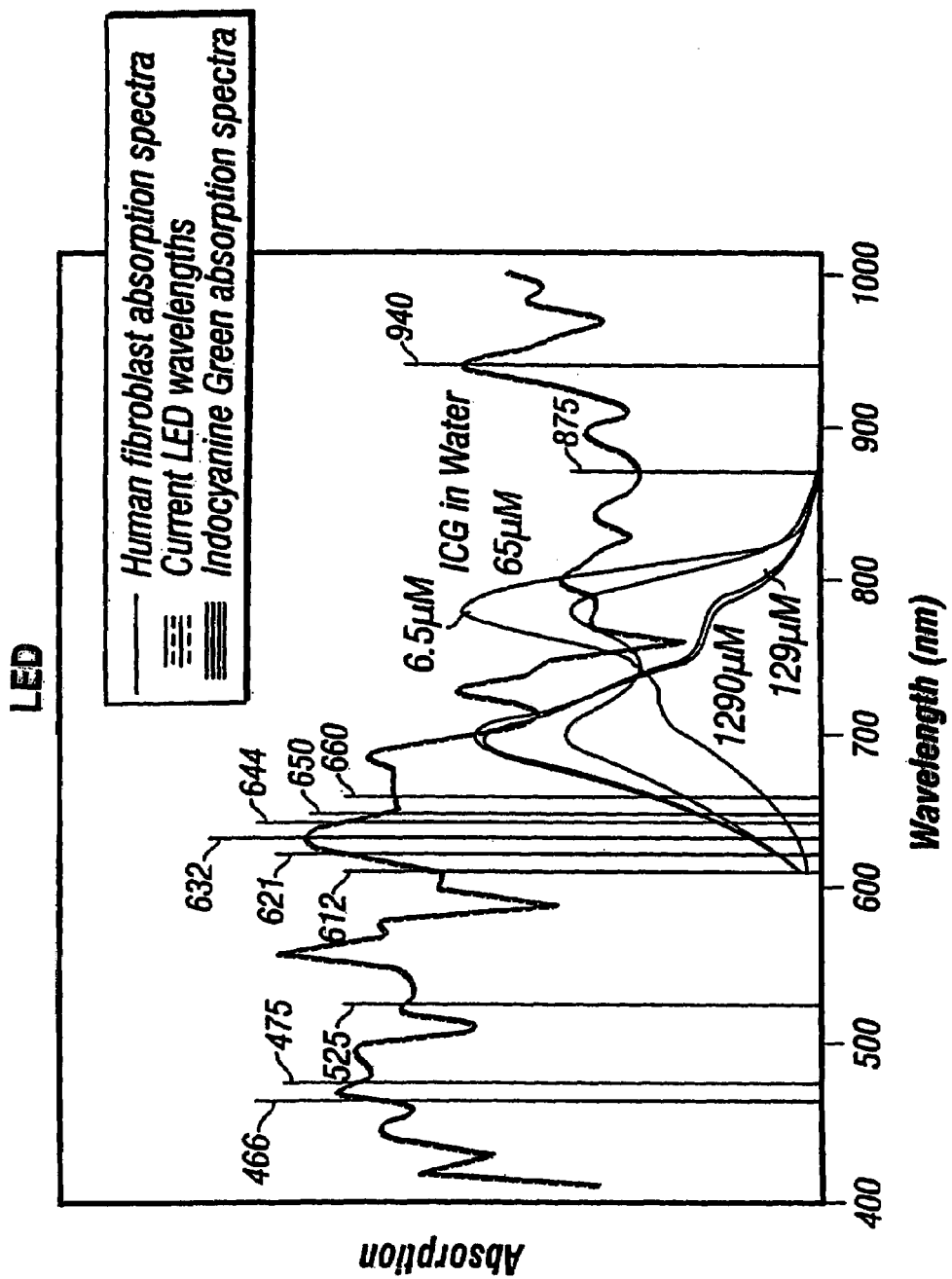
FIG. 12 shows the absorption spectrum for human fibroblast overlaid with the wavelengths of various, commercially produced LEDs, and also the absorption spectrum of indocyanine green.
Figure 13:
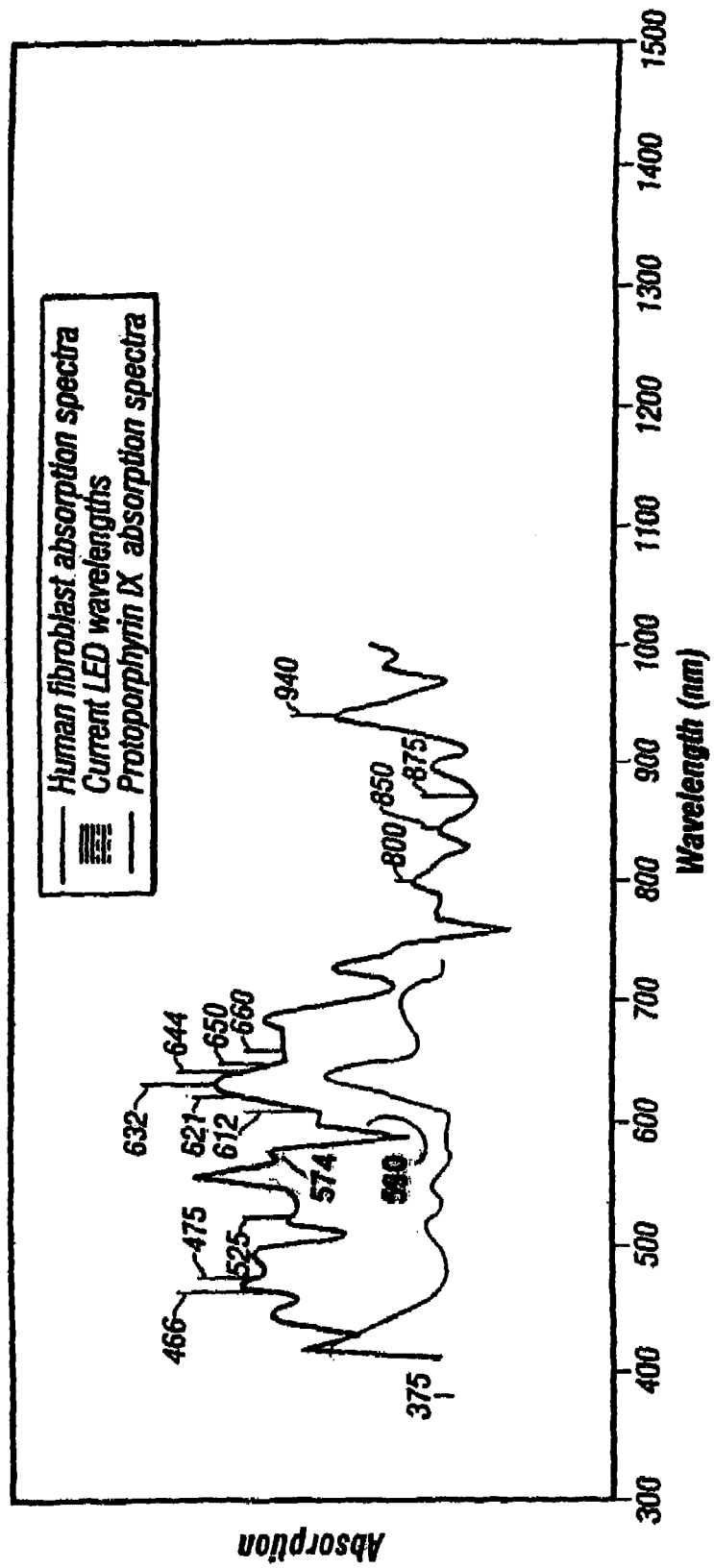
FIG. 13 shows the absorption spectrum for human fibroblast overlaid with the wavelengths of various, commercially produced LEDs, and also the absorption spectrum of protoporphyrin IX.

One preferred embodiment uses the transdermal application of chlorophyll to the sebaceous oil gland and surrounding tissue. The chlorophyll is then exposed to a source of electromagnetic radiation such as from a laser, an LED, a flash-lamp, or other source filtered to provide a dominant wavelength of from about 400 to about 450 nm. Other preferred wavelengths include from about 360 nm to about 440 nm and, with greater preference, from about 380 nm to about 420 nm. Pulse durations may be selected with sufficient power density to allow the target tissue to be appropriately inhibited to reduce acne bacteria content and to reduce or destroy gland activity through photomodulation and photothermal means. While blue light is used for illustrative purposes, it has been found that red light is also effective in accordance with the present invention. Generally, one skilled in the art will recognize to choose a light wavelength for treatment in the range of about 300 nm to about 1400 nm based on the absorption spectrum of the chromophore or other light-activated topical composition used. FIG. 7 shows the absorption spectrum for 0.03% Na Cu Chlorophyllin in deionized water. The primary absorption peak is shown to be at around 400 nm. This would indicate that for this chromophore, the most suitable wavelength for photomodulator and/or photothermal treatment would be at around 400 nm. Another absorption peak occurs at around 620 nm, thus in an instance where a light source with a dominant wavelength of around 400 nm was not available, a light source with a dominant wavelength of around 620 nm could be used. This figure further illustrates the absorption spectra of a carotenoid with a broad absorption band from 400 nm to 520 nm. This allows use of more wavelengths including those of green light (500 nm to 520 nm). A comparison of the absorption spectra of various naturally occurring chromophores is shown in FIG. 8.

One acne treatment process uses a solution of graphite in a carrier solution and a Q-switched 1064 nm ND:YAG laser. The solution may be applied to the skin which is then treated with the laser using known parameters. It may be preferable to use a high repetition rate and move the laser handpiece slowly enough that pulses are "stacked" in one spot for several pulses before the handpiece is moved to an adjacent spot. It has been found that there is a stair-step like effect of incremental temperature rise in the sebaceous glands with the second and third pulses versus a single pulse. A faster repetition rate also tends to help build the heat up faster, and to higher levels. This tends to produce the maximum heat (which is desirable, as long as the heat stays confined to the sebaceous glands and the immediately adjacent supporting tissues). Since this effect occurs substantially simultaneously with other destructive effects of the process, the damage to sebaceous glands tends to be enhanced. Unlike carbon exploded particles on light impact, the dyes and similar agents may actually remain absorbing for a brief time until they reach a critical temperature at which time they are destroyed or become non absorbers, thus acting as a sort of heat sink for a brief time, allowing more heat to accumulate than with carbon solutions and short pulsed Q-Switched lasers. Safety remains at about the same level, since dye related damage tends to be confined to target tissues. There is no appreciable change in patient treatment time.

Another preferred embodiment uses a longer pulsed laser in the 750 nm-1000 nm range and appropriate parameters to achieve the desired tissue damage goal.

Another embodiment uses a tissue dye which attaches to, or is incorporated into, a target cell and surrounding tissues. The target tissue may be illuminated with a multi-wavelength non-laser light source using appropriate parameters to achieve the desired tissue damage goal.

Another embodiment uses a light source which is well-absorbed by the melanin naturally present in skin and undyed darker hairs. Natural or synthetic melanin or derivatives thereof will be well-absorbed by the same wavelength of light (or alternatively two or more wavelengths, one for melanin and one or more for the dye). This melanin agent is delivered into the sebaceous gland, duct, or supporting tissue, resulting in an enhanced or greater injury to the target tissue (or permitting lower treatment energy parameters, resulting in safer treatment than if the sebaceous gland, duct, or supporting tissue were treated without the melanin dye). This tends to benefit people having darker skin or tanned skin, by allowing lower treatment energy. For example, a diode laser or LED or non-laser light source could produce a continuous or pseudo-continuous beam of light energy using pulse durations as long as seconds at a wavelength which is absorbed by the light-activated chromophore, native porphyrin containing acne bacteria porphyrin compound, or native sebaceous gland, duct, or supporting tissue pigment and also by the melanin or dye used. A pulse duration on the order of between about one and thirty seconds appears to be preferable. This also tends to be a much longer time than is used in most systems in use today.

Another embodiment uses an agent which facilitates cavitation shock waves or a thermal effect or both. This preferentially damages (or stimulates) the target tissues while minimizing damage (or other adverse effects) on surrounding non-target tissues. This may be used with very short pulsed lasers or light sources or with ultrasound alone.

In one embodiment a process in accordance with the present invention may be used to provide short or long-term control, improvement, reduction or elimination of acne or other related skin diseases. An active agent may be physically or chemically or immunologically incorporated into cells of the sebaceous (oil) glands, ducts, or supporting tissue, or into the naturally occurring acne bacteria, porphyrin compounds, naturally occurring light activated chromophores, yeast or similar organisms which feed on the oil in the oil glands (or sweat glands) or exists in the oil or oil glands as otherwise relatively benign inhabitants. Some acne bacteria may not inhabit all sebaceous structures and other strains may not produce native porphyrins to target with light. Other acne bacteria may be located deeper than 400 nm to 420 nm light can adequately penetrate, thus treatment with light alone may be only partially effective in clinical treatment. Improvement in skin disorders may be a direct or indirect result of the application of the agents in this process, as may reduced oiliness of the skin, reduced size or diminished appearance of pores, etc. The present invention is also useful for treating enlarged pores, oily skin, and other disorders where there is no active acne-related disorder.

Other similar disorders such as folliculitis which involve the pilosebaceous (hair/oil gland) unit may also be treated using the present invention. The present invention may also be used to reduce perspiration, sweating, or hyperhidrosis from eccrine (sweat) glands or apocrine glands. A preferred embodiment of the present invention may be used to treat or prevent other skin disorders such as, for example, viral warts, psoriasis, precancerous solar keratosis or skin lesions, hyperhidrosis/excessive sweating, aging, wrinkled or sun damaged skin, and skin ulcers (diabetic, pressure, venous stasis).

Scarring is commonly seen as a consequence of disorders, diseases, or dysfunctions of the sebaceous apparatus. Scarring may consist of one or more of the following: raised hypertrophic scars or fibrosis, depressed atrophic scars, hyperpigmentation, hyperpigmentary redness or telangectasia. Photomodulatory, photochemical, or photothermal treatments alone, or in combination with exogenous or endogenous chromophores, or combinations thereof, can be used simultaneously, sequentially, etc., as described herein for the treatment of sebaceous gland disorders, diseases, or dysfunctions. Further, as herein described, the term photomodulation refers to the treatment of living tissue with light along, heat emitted by a light source, or light-activated chemical compositions, or any combination thereof. Falling within the scope of photomodulatory treatments are photothermal treatment, photoactivation, photoinhibition, and photochemical treatment of living tissue and, in particular, sebaceous structures within human skin. Further, electromagnetic emitters of the present invention can fall into three categories: those which emit light in the visible spectrum and are useful for photoactivation and photoinhibition photomodulatory process; those that emit light in the ultraviolet spectrum and are also useful for photoactivation and photoinhibition photomodulatory process; and those that emit light in the infrared region and permit photomodulation treatment to be carried out through photothermal means, i.e., heat activation of the exogenous chromophore, living cells or tissue, or both.

A preferred embodiment of the present invention may use various microencapsulation processes to deliver active agents. If the diameter of the micro encapsulations is about five microns, then there may be relatively site specific preferential delivery into the sebaceous oil glands or skin surface stratum corneum cells. If the diameter of the microencapsulations is in the range of about one micron, then the active agents may be delivered with a more random distribution between the hair ducts and the oil glands. If the diameter of the microencapsulations is larger, on the order of about 20 microns or greater, then delivery will tend to be restricted primarily to the skin surface. The micro encapsulations may be synthetic or natural. If ultrasound is used to enhance penetration, then the diameters and ultrasound treatment parameters may need to be adjusted according to the applicable principles which allow the estimation of the optimal ultrasound parameters for driving small particles into the skin, skin appendages or skin orifices.

Microencapsulation may be used to improve delivery of known agents such as chlorophyll, carotenoids, methylene blue, indocyanine green and particles of carbon or graphite. A known technique for using a laser to produce a wavelength that may be absorbed by indocyanine green for a hair removal treatment process is described, for example, in U.S. Pat. No. 5,669,916, which is incorporated by reference. It has been found that by using smaller particles and putting the smaller particles into more uniform diameter microencapsulations, more site specific or uniform targeting may be achieved. A preferred formulation may include indocyanine green or other dyes or agents to form a lipid complex which is fat-loving (lipophilic). The delivery and clinical effects of agents and dyes such as indocyanine green dye may be refined and enhanced by selecting a carrier or encapsulation having a diameter that increases the probability of preferential delivery to a desired space, and/or that enables interaction with ultrasound to thereby increase the probability of preferential delivery, and/or that selectively attaches to the sebaceous gland, duct, supporting tissues, oil itself or bacteria, yeasts, or other organisms residing within these tissues.

Indocyanine green dye is presently in medical use, appears to be relatively benign, may be activated by red visible lasers, or other source of monochromatic or multichromatic light, (in the 800 nm range) may penetrate deeply enough to reach the oil glands, is used for leg vein and hair removal, and is relatively safe, cheap, and reliable. A known technique for using a laser to produce a wavelength that may be absorbed by indocyanine green for use in a leg vein treatment process is described, for example, in U.S. Pat. No. 5,658,323, which is incorporated by reference. Methylene blue has also been used according to the present invention with good success.

The microsponges containing the active agent may selectively attach, or at least have a chemical affinity for, some part of the oil gland. The ICN dye may be conjugated with lipids, which would then have an affinity for the oil glands. Alternatively, the attachment may occur after the active agent is released from the microsponge, either passively or by attractive or chemical forces. In the case of some microencapsulation carrier vehicles, release may occur after disruption of the vehicle integrity itself, possibly by ultrasound or laser or light or other energy source or perhaps a chemical reaction.

In a preferred embodiment the ICN dye may be mixed with lipids, or put into microsponges (a.k.a. microspheres), and then applied to the skin surface, allowed to sit for a time. Excess dye may be removed, and then the area may be treated with laser light at about 800 nm, between about 0.1 and 100 millisec pulses and around 1.0-10.0 Joules/cm$^2$.

U.S. Pat. No. 5,817,089 specifies "particles having a major diameter of about 1 micron". It has been discovered, however, that these diameters may not be optimal. A 1993 Pharmaceutical Research journal article by Rolland et al describes an acne treatment wherein a topical acne drug is delivered with less irritation by putting the drug into synthetic polymer microsphere sponges. This article reported that an optimal diameter for site-specific delivery into sebaceous oil glands in the skin was about 5 microns, and that 1 micron particles randomly delivered to the hair follicle and stratum corneum.

Most agents may not inherently be the optimal size. However, virtually any agent may be preferentially delivered to the sebaceous glands by either synthetic microspheres, or liposomes, or albumen microspheres, or other similar "delivery devices".

In a preferred embodiment for treatment of acne, graphite particles having an average diameter of about one micron may be placed in delivery devices, such as microsponges, having an average diameter of about five microns. The microsponges may then be suspended in a lotion. Ultrasound may be used to drive the particles into the skin. The optimal ultrasound parameters may be based on the outside particle diameter (especially if particles are uniform). Selective delivery of the particles to hair and perhaps to sweat glands may be improved.

Use of such applications could enable selective delivery of anti-acne agents, or hair dye for laser hair removal, or agents which stimulate hair growth, or other hair treatments, where the encapsulation diameter was used, with or without ultrasound, to preferentially deliver, and ultrasound at different parameters or laser was used to release (not necessarily to activate or interact).

These techniques may be applied to many other agents in addition to ICN dye and graphite lotions. The term "encapsulated delivery device" is used herein as a generic term which encompasses all such possible items.

Pressure may be used to impel particles (i.e., graphite, carbon, or other active agent or skin contaminant particulates) into the skin, either in the spaces between the stratum corneum, into the hair ducts and hair follicles, the sebaceous oil glands, or other structures. Air pressure or other gases or liquids may be used to enhance delivery or increase the quantity of delivered agent. A known technique for using an air pressure device for removing skin surface is described, for example, in U.S. Pat. No. 5,037,432, which is incorporated by reference.

Ultrasound may be used to physically deliver hair dye and to enhance penetration into the hair shaft itself (see, for example, U.S. Pat. No. 5,817,089, incorporated herein by reference). The use of ultrasound to physically drive graphite particles down for the treatment of unwanted hair or acne appears to have been suggested in the prior art. However, the applicant is aware of no prior art disclosure or suggestion of: (1) the use of ultrasound to enhance the penetration of an agent into the hair shaft itself, or into surrounding cells; (2) the use of ultrasound to drive graphite particles into spaces between the stratum corneum to enhance the effects of a skin peel process (which physically removes a portion of the outer layers of the skin surface); or (3) physically removing the hair by methods such as waxing or pulling and then injecting the treatment composition, i.e., the chromophore or other topical composition, into the sebaceous gland or duct. Such methods are contemplated in one embodiment of the invention.

A known skin peel process may be improved by using ultrasound to open intercellular spaces in the outer stratum corneum layer of the skin via cavitation. Then an active agent may be driven in further with the same or similar ultrasound. Fibroblast stimulation may be optimized with both topical agents that are applied afterwards (while the skin is still relatively permeable) and also with additional low level light stimulation.

The processes described above may be used to deliver two different agents, either serially or simultaneously. The two agents may then be activated by the light source together to work synergistically, or to combine and then have an effect, or to deliver two different agents that may be activated simultaneously or very closely in time. Two different light sources or wavelengths may be used serially or simultaneous to have different effects such as treating active acne lesions and also acne scarring; treating acne rosacea lesions and also rosacea blood vessels or telangectasia; or using photothermal means for active acne and nonthermal photomodulation for treating acne scarring or skin wrinkles.

Two entirely different laser, LED, or light beams may be delivered substantially simultaneously through the same optics at different parameters. For example, one beam may be delivered primarily to release or to activate, and a second beam primarily to treat. Additive effects may be achieved by using two beams at the same time, such as the use of blue light with a wavelength of approximately 400 nm and red light with a wavelength of approximately 600 nm. For example, a known process for skin peel and hair reduction may be optimal at 1064 nm for safety and for treating all skin colors, but other wavelengths may be better to achieve a low level laser stimulation of fibroblasts. Acne reduction is achieved by this process, as well, using lasers or LEDS as the low-level light source at a wavelength chosen according to the absorption spectrum of the topical composition used. Particularly preferred for topical compositions are those comprising naturally occurring chlorophyll-containing compounds, carotenoid-containing compounds, derivatives thereof, and mixtures thereof, as well as derivatives, analogs, and genetically engineered forms of such agents.

A hand-held device containing the low-level light source may be used to photomodulate or photothermally activate, or both, the living tissue or active ingredient in the topical composition, or both, for skin peel, hair reduction, or acne reduction, and either simultaneous or synchronized sequentially in time to deliver another wavelength that may be optimal to in view of the absorption characteristics of the patient's fibroblast spectrum or the spectrum of the topical composition. In the one case it may be the best wavelength to stimulate fibroblasts. In another case it may allow selection of a melanin or dye (or other agent) having very strong affinity for the sebaceous gland and very strong absorption at the wavelength used for prevention or treatment.

There are a wide variety of different operating parameters that may comprise conditions effective to produce beneficial cellular effects such as triggering cellular regeneration or photoactivation or photoinhibition which, for example, could reduce the activity of, or even destroy, oil glands in the skin, thereby indirectly reducing acne bacteria. Also, it is preferable to target a natural chromophore for photoactivation or photoinhibition, each falling under the general term photomodulation is possible for directly treating the naturally occurring porphyrin compounds in acne bacteria, in addition to targeting exogenous chromophores like carotenoids, chlorophyll and its derivatives including copper chlorophyllin and other dyes such as indocyanine green dye, methylene blue dye, and similar compositions known to those skilled in the art. Further photothermal modulation of the oil glands and surrounding tissue can be accomplished via the same means as described above, although the operating parameters may vary. The difference being that photothermal treatment uses heat to induce minor to moderate amounts of thermal injury to the gland or surround tissue to reduce the activity of the target tissue or destroy it altogether.

Exogenous chromophores are substances which absorb light or electromagnetic radiation in at least one narrow band of wavelengths and assist with the treatment method and system of the present invention by applying them to an area of the skin to be treated. Selection of the exogenous chromophore is determined by the absorption spectra of the chromophores and is dependent on the wavelength of the narrowband multichromatic emitter used for treatment. In accordance with a preferred embodiment of the invention, the chromophore will aid in treatment by enabling at least the dominant or central wavelength of the narrowband, multichromatic radiation to penetrate at least the stratum corneum layer of the skin and permitting the photomodulation or photothermal injury or destruction of living tissue, sebaceous oil gland, duct, or supporting tissue in and below the stratum corneum. In some instances, the photomodulated tissue can be below all of the epithelial layers of the skin.

Some examples of possible operating parameters may include the wavelengths of the electromagnetic radiation to which the living tissue containing cells to be regenerated, stimulated, inhibited, or destroyed, the duration of pulses (pulse duraction) of the electromagnetic radiation, the number of pulses, the duration between pulses, also referred to as repetition rate or interpulse interval. Intervals between treatments can be as long as hours, days, weeks, months, etc.; and the total number of treatments is determined by the response of the individual patient. Further, treatment regimens using a combination of more than one wavelengths either simultaneous or in sequence may be used. As well, the energy intensity of the radiation as measured at the living tissue (typically measured in Joules per centimeter squared, watts per centimeter squared, etc.), the pH of the cell, tissue or skin, the skin temperature, and time from application to treatment with a light source, if used with exogenous chromophore (which can be topical, injected, driven in with ultrasound, or systemic) is determined by the nature of the treatment and is further illustrated in the Examples.

Wavelength—Each target cell or subcellular component, or molecular bond therein, tends to have at least one unique and characteristic "action spectrum" at which it exhibits certain electromagnetic or light absorption peaks or maxima FIG. 3, for example, shows the absorption spectrum of one line of human fibroblast cells in monolayer tissue culture. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with an absorption maxima for the target cell or subcellular component or tissue, or exogenous chromophore. In some cases it may be desirable to target more than one maxima—either simultaneously or sequentially on the same or different treatment dates. The presence of multiple maxima action spectra are common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present invention, in contrast to the use of multiple narrowband emitters. The laser diodes are also multichromatic with narrow wavelength bands around a dominant band, i.e., they are narrowband multichromatic devices—devices which emit electromagnetic in a narrow band of radiation either symetrically or asymetrically around a dominant wavelength. For purposes of the present invention, any device that emits electromagnetic radiation in a bandwidth of +/−about 1000 nanometers around a dominant wavelength can be considered to be a narrowband, multichromatic emitter. LEDS, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. The use of lasers, according to the prior art, has relied upon the coherent, i.e., monochromatic, nature of their electromagnetic emissions.

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method. It is also important to penetrate any interfering chromophore that also absorbs at this same wavelength (e.g. dark ethnic skin, plastic Petrie dishes for tissue or cell culture, etc.). It is important to penetrate any tissues or organs in its pathway.

For example, light having a dominant wavelength emission in the range of about 400 nm to about 420 nm has such a short wavelength that not all sebaceous glands or acne cysts can be effectively treated due to the limited depth of penetration of the radiation, whereas light having a wavelength of about 600 nm to about 660 nm can more easily penetrate to a greater depth, if treatment of the lower dermal layers or even deeper is desirable. Accordingly, the selection of the dominant wavelength of the radiation emitter is also dependent on the depth of treatment desired. The selection of the proper wavelength is one of the significant parameters for effective use of the present invention, but others are important as well:

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation.

Pulse duration—The exposure time for the irradiation is very critical and varies with the desired effect and the target cell, subcellular component, exogenous chromophore tissue or organ (e.g. 0.5 microseconds to 10 min may be effective for human fibroblasts, though greater or lesser may also be used successfully).

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others.

Frequency (if pulsed)—e.g. higher frequency tends to be inhibitory while lower frequency tends to be stimulatory, but exceptions may occur.

Duty cycle—This is the device light output repetition cycle whereby the irradiation is repeated at periodic intervals, also referred to herein as the interpulse delay (time between pulses when the treatment session comprises a series of pulses).

Suitable active agents for use in topical compositions applied to the skin in accordance with the present invention include one or more of Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, bacteriochlorophyll, copper chlorophyllin, chloroplasts, carotenoids, phycobilin, rhodopsin, anthocyanin, and derivatives, subcomponents, immunological complexes and antibodies directed towards any component of the target skin structure or apparatus, and analogs of the above items both natural and synthetic, as well as combinations thereof.

While not a limiting factor, a common aspect of the most useful natural chromophores of the present invention is found in their chemical structure. Naturally occurring chromophores have a metal-ligand bonding site. FIG. 2 illustrates the chemical structure of chlorophyll a, characterized by $R=CH_3$. A magnesium atom is present at the metal-ligand bonding site in the FIG.ure. Chlorophyll a exhibits absorption maxima at 409 nm, 429 nm, 498 nm, 531 nm, 577 nm, 613 nm, and 660 nm. Chlorophyll b is characterized by $R=CHO$ exhibits absorption maxima at 427 nm, 453 nm, 545 nm, 565 nm, 593 nm, and 642 nm. It can be readily seen that various types of chlorophyll, or combinations thereof, can be used as topically applied chromophores to assist the absorption of certain wavelengths of light delivered through the skin or soft tissue for various treatments. When used to enhance the absorption of a wavelength of light that coincides with an absorption maxima of target cells such as human fibroblasts, treatment can be even more effective or can be carried out with reduced light intensities or can produce multiple beneficial effects, such as treating acne bacteria and reducing or eliminating acne scarring.

The alkaline hydrolysis of chlorophyll opens the cyclopentanone ring and replaces the methyl and phytyl ester groups with sodium or potassium. These resulting salts are called chlorophyllins and are water soluble. The alkaline hydrolysis of the chlorophyll shown in FIG. 2 will result in a NaMg Chlorophyllin, but other salts can easily be formed by replacing the Mg atom in the chlorophyll with other metals or reactive transition metals, for example, such as copper, aluminum, iron, metal chelates, or antibody complexes. Such a substitution is made by treating the chlorophyll with an acid causing the Mg to be removed and replaced by $H_2$ which, in turn, is easily replaced by other metals.

Unlike artificially synthesized chromophores, naturally occurring chromophores bear the similar attribute of having the metal ligand bonding site which will dissociate the metal ion upon treatment with an acid. The acid content of human skin is sufficient to trigger this reaction and, in turn, cause the chlorophyll, having lost the metal ion, to become less soluble in water. The resulting chlorophyll, or other naturally occurring agent that dissociates a metal ion from a ligand bond under acidic conditions such as porphyrin for example, makes an excellent topical composition with superior optical properties for acting as a chromophore to enhance low-intensity light therapies. In another embodiment of the invention, therefore, the preferred chromophore is a compound having a metal ligand bond that dissociates the metal ion under acidic conditions. In one embodiment of the invention, topical skin care formulations may be used for altering the pH or acidity of the skin.

In addition to being an effective treatment method for reducing and eliminating the presence of common acne bacteria such as acnes vulgaris and for safely treating conditions such as pseudofolliculitis barbae, acne rosacea, and sebaceous hyperplasia, the present invention also has application to the reduction of cellulite. Using any of the light sources suitable for use as described herein, adipocyte cells can be photomodulated. Photomodulation increases the local microcirculation in the cellulite and alters the metabolic activity of the cells. Enhanced local microcirculation, metabolism or enzymation activity, or combinations thereof, may be produced by photomodulatory means. To enhance the treatment, any of the topical chromophores as previously described can be used or non-chromophoric compositions can be used in conjunction with any of the photomodulatory methods, including low-intensity light therapy. Further photothermal means may be used to destroy adipocyte cells alone or in combination with photomodulatory means, with or without the use of exogenous chromophores.

Many living organisms—both animals and plants—have as one of their major defense mechanisms against environmental damage to their cells and DNA repair system. This system is present in many if not all living organisms ranging from bacteria and yeasts to insects, amphibians, rodents and humans. This DNA mechanism is one which is involved in processes to minimize death of cells, mutations, errors in copying DNA or permanent DNA damage. These types of environmental and disease and drug related DNA damage are involved in aging and cancer.

One of these cancers, skin cancer, results from ultraviolet light damage to the DNA produced by environmental exposure to natural sunlight. Almost all living organisms are unavoidably exposed to sunlight and thus to these damaging UV rays. The damage which is produced is a change in the structure of the DNA called pyrimidine dimmers. This causes the DNA structure to be altered so that it cannot be read or copied any longer by the skin cells. This affects genes and tumor development and proper functioning of the immune system.

An enzyme called photolyase helps to restore the original structure and function of the damaged DNA. Interestingly photolyases are activated by light . . . to then act to repair the DNA damaged by ultraviolet light. In the dark it binds to the cyclobutane pyrimidine dimmer created by the UV light and converts it into two adjacent pyrimidines (no dimer connecting these any longer) and thus the DNA damage is repaired. This direct reversal of DNA damage is called "photoreactivation". The photolyase upon exposure to blue light absorbs the light energy and uses this energy to 'split' the dimer and thus restore the normal DNA structure. Other mechanisms of DNA repair exist as well.

The photolyase repair mechanism is not well understood at present, but naturally occurring or synthetic or genetically engineered photolyase from essentially any living organism source can be utilized for other organisms including human and veterinary and plant applications. DNA damage produced by factors other than ultraviolet light may also be repaired including, but not limited to, such factors as other environmental damage or toxins, radiation, drugs, diseases, chemotherapy for cancer, cancer, microgravity and space travel related damage, and a myriad of other causes.

The use of such naturally derived or artificially created or genetically engineered photolyase enzymes or related enzymes or other proteins functioning for DNA or RNA repair have a wide variety of applications. For example, the ability to treat skin damaged by sunlight/ultraviolet light of disease and to repair, reverse, diminish or otherwise reduce the risk of skin cancer could be used either as a therapeutic treatment or as a preventive measure for people with severely sundamaged skin, with precancerous skin lesions, or with skin cancer.

This principle applies not only to skin cells and skin cancer but to a very broad range of skin and internal disorders, diseases, dysfunctions, genetic disorders, damage and tumors and cancers. In fact potentially any living cells might have beneficial effects from treatment with photolyase or similar proteins in combination with light therapy.

While in nature the light to activate the photolyase typically comes from natural sunlight, essentially any light source, laser and non laser, narrow band or broader bandwidth sources can activate the photolyase if the proper wavelengths and treatment parameters are selected. Thus natural sunlight filtered through a selective sunscreen could be used to activate both native and exogenously applied photolyases. Another treatment option would be to apply the photolyase and then treat with a controlled light source exposure to the proper wavelength band and parameters. A wide variety of light sources could be utilized and the range of these is described elsewhere in this application. For example a low energy microwatt narrow band but multispectral LED light source or array with mixed wavelengths could be utilized. Another embodiment is a filtered metal halide light source with a dominant wavelength of 415 nm+/−20 nm and an exposure of 1-30 minutes at 1-100 milliwatts output can be utilized. Such exposure would occur minutes to days after application of a topical product containing photolyase.

Another example would be the repair of cells in the skin which have environmental damage but instead of repairing the cells which lead to skin cancer the cells which lead to aging (photoaging) of the skin are targeted for this therapy. In one embodiment, kin fibroblasts which have been sun damaged are treated with a photolyase and subsequently the photolyase is photomodulated with blue light to set in motion the DNA repair mechanism of photolyase—that is photoreactivation. This allows the repair of the structure and thus the normal functioning of the fibroblast DNA thus allowing normal functioning and proliferation of these fibroblasts—which produce the proteins such as collagen and elastin and hyaluronic acid and matrix ground substance which cause skin to be firm and elastic and youthful in appearance—thus producing anti-aging or skin rejuvenation effects in the skin as well as improving the structure and healthy function of the skin.

Various cofactors which are involved in this photoreactivation process can also be added either topically or systemically to further enhance or improve the efficiency of this process. Other cofactors needed in the production of these proteins once the cells recover normal function also may be added topically or systemically to enhance the anti-aging or skin rejuvenation process. The delivery of both the photolyase and/or the cofactors described above can be enhanced by utilizing ultrasound to increase skin permeability or to increase transport across the skin barrier and into the skin and underlying tissues. Removal of a portion of the stratum corneum of the skin can also be used, alone or in combination with ultrasound, to enhance penetration and delivery of these topically applied agents. Additionally such methods of removing or altering the stratum corneum can assist in penetration of the light or the efficiency of same or allow use of lower powered light sources including home use devices such as battery powered LED sources.

A variety of sources exist for obtaining photolyases. These may include native naturally occurring photolyases, compounds derived from other living organisms (that is one may use for example bacterially derived, or yeast derived, or plankton rederived, or synthetic or genetically engineered, etc., photolyases and use them in human skin for beneficial effects thus not limited to same species derived photolyases. One known photolase is derived from Anacystis nidulans while others can be derived from bacteria—yeast in fact protect themselves with a photolyase which can be used in humans, other microorganisms, plants, insects, amphibian and animal sources exist.

The photolyase enzymes function by light induced electron transfer from a reduced FAD factor to the environmental exposure produced pyrimidine dimers. The use of free radical inhibitors or quenchers such as antioxidants can also be used to supplement the photolyase therapy. Other light activated chromophores may be utilized with light sources and properly selected parameters to further enhance, stimulate, photomodulate, photoactivate or photoinhibit the target or supporting cells or tissue to promote the most effective treatment.

There are many causes of free radical damage to cells. In one embodiment wound healing can be accelerated by utilizing a combination of antioxidants, cell growth factors, direct photomodulation (photoactivation) of cells, and photoreactivation through photolyases. Topical or systemic therapy with the proper cofactors and replacing any deficiencies of cofactors can further enhance wound healing. For example, a chronic leg ulcer wound could be treated with an antioxidant mixture of vitamin E, vitamin C and glutathione, as well as cofactors such as fatty acids and keto acids and low level light therapy using and LED array with parameters selected to photostimulate fibroblasts and epithelial cells could also receive treatment with a photolyase and blue light therapy thus greatly accelerating wound healing and healing wounds or burns that would otherwise not be treatable.

The potential uses of photolyases and light therapy include: the treatment or repair or reverse nerve damage or diseases including spinal cord injuries and diseases; cancer or cancer treatment related problems including radiation and chemotherapy; cervical dysplasia and esophageal dysplasia (Barrett's esophagus) and other epithelial derived cell or organ disorders such as lung, oral cavity, mucous membranes, etc.; eye related diseases including but not limited to macular degeneration, cataracts, etc.

There are very broad health and commercial applications of photolyase mediated photorepair or photoreactivation of DNA (or RNA) damage with flavin radical photoreduction/DNA repair via photomodulation or native or exogenously applied natural or synthetic or genetically engineered photolyases. The addition of topical. Oral, or systemically administered photolyases and also their cofactors or cofactors of the cells whose DNA is being repaired further enhance these applications. The enhanced delivery of such substances topically via ultrasound assisted delivery, via alteration of the skin's stratum corneum, and/or via special formulations or via special delivery vehicles or encapsulations are yet an additional enhancement to this process.

There are also blue light photoreceptors such as cryptochrome which photomodulate the molecular clocks of cells and the biological or circadian rhythm clocks of animals and plants—that is the mechanism which regulates organism response to solar day/night rhythms in living organisms. These protein photoreceptors include vitamin B based crytochromes. Humans have two presently identified cryptochrome genes—which can be directly or indirectly photomodulated (that is photoactivated or photoinhibited).

The clinical applications include treatment of circadian rhythm disorders such as 'jet lag', shift work, etc, but also insomnia, sleep disorders, immune dysfunction disorders, space flight related, prolonged underwater habitation, and other disturbances of circadian rhythm in animals. Circadian issues also exist for many other living organisms including the plant kingdom.

Warts can be treated using exogenous or endogenous chromophores with either photothermal or non thermal photomodulation techniques—or a combination of both. Examples of preferred embodiments of endogenous chromophores include the targeting of the vascular blood supply of the wart with either method. Anther preferred embodiment is the use of a topically applied or injected or ultrasonically enhanced delivery of such a chromophore into the wart or its blood supply or supporting tissues with subsequent photomodulation or photothermal activation of the chromophore.

One such example would be that of a chlorophyll topical formulation similar to those described elsewhere in this application but of higher concentration and vehicle and particle size optimized for wart therapy and the anatomic location of the warts (for example warts on the thicker skin of the hand might be formulated differently than that used for vaginal warts). An LED light source could be used for home use with 644 nm in a battery powered unit wherein the topical formula was applied daily and treatment of individual warts was performed with the proper parameters until the warts disappeared.

For the situation of vaginal warts, a cylindrical device with an array of LED arranged and optically diffused such that the entire vaginal cavity could be properly illuminated in a medically performed procedure would represent another embodiment of this therapy. A wide range of substances can be utilized either as the primary chromophore or as adjunctive supporting therapy. These compounds are listed elsewhere in this application. In another embodiment an immune stimulator is utilized in conjunction with photomodulation with or without an exogenous chromophore. In yet another embodiment a higher powered light source either narrow or broad band can be utilized with the same chromophore therapy as outlined above, but with parameters selected so that the interaction with the chromophore is non photomodulation, but rather intense photothermal effect so as to damage or destroy the wart but with minimal damage to surrounding uninvolved and non supporting tissues.

In one embodiment a chlorophyll and carotenoid topical formulation is applied and natural sunlight with or without a selective sunscreen are used to interact with the topical formulation. Another embodiment utilizes an injected or ultrasonically enhanced topical delivery of a dye such as indocyanine green which has been used for vascular injections safely in other medical applications.

Papulosquamous, eczematous and psoriasiform and related skin disorders can be improved, controlled, reduced or even cleared by the same photomodulation or photothermal interaction with endogenous or exogenous chromophores. The process outlined for warts and the other disorders in this application may be used for such therapies. The use of ultrasound is particularly useful in the more scaly disorders in this group of diseases as are enzyme peels and other methods with gently remove scaling skin. Penetration of light into psoriasis presents for example a major problem with current therapies. Penetration of drugs and topical agents is likewise a major therapeutic challenge. If the dry skin on top of psoriasis is removed it is well known that this stimulates further growth of the plaque or lesion of psoriasis—yet removal is needed to allow the drugs to penetrate and for light to penetrate. Currently almost all psoriasis light therapy is ultraviolet light and thus the risk of skin cancer and also of photoaging is very significant with a lifetime of repeated ultraviolet light therapy. Also such therapy typically involves treating large areas or even the entire body (standing in a large light therapy unit is like being in a tanning bed which is standing upright). Thus not only does the skin with psoriasis lesions get treated, but also all the normal uninvolved skin typically gets exposed to the damaging ultraviolet light.

Furthermore typical psoriasis treatments involve the use of oral drugs called psoralens. These drugs cross link DNA and are light activated. Thus DNA damage in produced not only by the ultraviolet light itself (like being out in sunlight but primarily ultraviolet A light), but in addition the psoralen drug produced DNA damage. Safety in children in an obvious concern as is use in pregnant or childbearing women.

The use of a topical light activated exogenous chromophore such as most of the agents listed in this application present no risk of DNA damage and also are generally very safe products—many are natural such as chlorophyll and can be safely used in children and pregnancy and child bearing age women. In addition the treatment is only activated where the topical agent is applied—unlike the use of oral psoralen drugs that activate not only the entire skin but also the retina and other tissues. The light used for this therapy is not only low in power, but it is for the most part visible or infrared light and is not ultraviolet—producing no DNA damage.

Thus the use of photomodulation or photothermal activation of exogenous light activated chromophores such as described herein represents a significant advance in safety and efficacy.

The photolyase embodiments described above also have some application for diseases such as psoriasis. For some cases of psoriasis are very extensive covering large amounts of the surface area of the body and may be resistant to other known therapies. The application of a topical formulation to the areas not being treated—or to all the body areas exposed to the traditional psoriasis phototherapy could receive a post treatment with the photolyase and blue light therapy—think of this as a type of 'antidote' to the ultraviolet psoriasis phototherapy wherein the repair of DNA damage to normal tissue was facilitated immediately following the psoriasis therapy—thus reducing significantly the risk of skin cancer and photoaging in future years.

Another embodiment involves the use of such a photolyase preparation in the evening after returning from a long day of occupational sun exposure or after an accidental sunburn. A spray or lotion containing the photolyase could be applied and then photorepair/photoreactivation of the acutely damaged DNA in the skin could be performed—and this could be performed with a large beam diameter home therapy unit—of by a white light source which contained enough of the desired wavelength at the proper parameters to produce this reaction. Additionally an antioxidant skin formulation could be also applied to minimize erythema and other undesired effects of the sunburn. One such embodiment would be the preparation described earlier with a combination of vitamin C, vitamin E and glutathione and free fatty acids and one or more keto acids. A similar formulation could contain these agents but utilize only one or two of the three antioxidants listed.

In vitro fertilization processes can also be enhanced by photomodulation—with or without an exogenous chromophore. This can simply target the cells or subcellular components themselves, as described in the applicants copending U.S. patent application Ser. No. 09/894,899 entitled "Method and Apparatus for Photomodulation of Living Cells", which is hereby incorporated by reference in its entirety.

This can result in a greater success rate of fertilization and/or growth of embryos or other desirable effects on this process. In one embodiment an LED light source is used to treat sperm of animals or humans or genetically engineered embryos or subcomponents thereof to enhance fertilization.

In another embodiment photolyase or other photoreparative or light activated DNA repair proteins or substances combined with photomodulation can be utilized to 'correct' DNA damage in embryonic tissues thus generating a normal or more normal embryo. This can be performed in vitro or in utero (utilizing tiny fiber optic delivery of the proper light parameters—or the light can be delivered from outside the body into the womb without the risk of introducing a fiber optic device.

Another process in which photomodulation can be utilized for significant benefit is in the stimulation of proliferation, growth, differentiation, etc of stem cells from any living organism. Stem cells growth and differentiation into tissues or organs or structures or cell cultures for infusion, implantation, etc (and their subsequent growth after such transfer) can be facilitated or enhanced or controlled or inhibited. The origin of such stem cells can be from any living tissue or organism. In humans stem cells for these embodiments may come from any source in the human body, but typically originate from the bone marrow, blood, embryo, placenta, fetus, umbilical cord or cord blood, and can be either naturally or artificially created either in vivo, ex vivo or in vitro with or without genetic alteration or manipulation or engineering. Such tissue can come from any living source of any origin.

Stem cells can be photoactivated or photoinhibited by photomodulation. There is little or no temperature rise with this process although transient local nondestructive intracellular thermal changes may contribute via such effects as membrane changes or structured conformational changes.

The wavelength or bandwidth of wavelengths is one of the critical factors in selective photomodulation. Pulsed or continuous exposure, duration and frequency of pulses (and dark 'off' period) and energy are also factors as well as the presence, absence or deficiency of any or all cofactors, enzymes, catalysts, or other building blocks of the process being photomodulated.

Photomodulation can control or direct the path or pathways of differentiation of stem cells, their proliferation and growth, their motility and ultimately what they produce or secrete and the specific activation or inhibition of such production.

Photomodulation can up-regulate or down-regulate a gene or group of genes, activate or inactivate enzymes, modulate DNA activity, and other cell regulatory functions.

Our analogy for photomodulation of stem cells is that a specific set of parameters can activate or inhibit differentiation or proliferation or other activities of a stem cell. Much as a burglar alarm keypad has a unique 'code' to arm (activate) or disarm (inhibit or inactivate) sending an alarm signal which then sets in motion a series of events so it is with photomodulation of stem cells.

Different parameters with the same wavelength may have very diverse and even opposite effects. When different parameters of photomodulation are performed simultaneously different effects may be produced (like playing a simple key versus a chord on a piano). When different parameters are used serially or sequentially the effects are also different—in fact depending on the time interval we may cancel out the prior photomodulation message (like canceling burglar alarm).

The selection of wavelength photomodulation is critical as is the bandwidth selected as there may be a very narrow bandwidth for some applications—in essence these are biologically active spectral intervals. Generally the photomodulation will target flavins, cytochromes, iron-sulfur complexes, quinines, heme, enzymes, and other transition metal ligand bond structures though not limited to these.

These act much like chlorophyll and other pigments in photosynthesis as 'antennae' for photo acceptor molecules. These photo acceptor sites receive photons from electromagnetic sources such as these described in this application, but also including radio frequency, microwaves, electrical stimulation, magnetic fields, and also may be affected by the state of polarization of light. Combinations of electromagnetic radiation sources may also be used.

The photon energy being received by the photo acceptor molecules from even low intensity light therapy (LILT) is sufficient to affect the chemical bonds thus 'energizing' the photo acceptor molecules which in turn transfers and may also amplify this energy signal. An 'electron shuttle' transports this to ultimately produce ATP (or inhibit) the mitochondria thus energizing the cell (for proliferation or secretory activities for example). This can be broad or very specific in the cellular response produced. The health of the cells and their environment can greatly affect the response to the photo modulation. Examples include hypoxia, excess or lack or ration of proper cofactors or growth factors, drug exposure (e.g. reduced ubiquinone from certain anticholesterol drugs) or antioxidant status, diseases, etc.

The as yet unknown mechanism, which establishes 'priorities' within living cells, can be photomodulated. This can include even the differentiation of early embryos or stem cell population. Exogenous light activated chromophores may also be used alone or in combination with exogenous chromophores. Genetically altered or engineered stem cells or stem cells which have an inborn genetic error or defect or uncommon but desirable or beneficial trait may require a different 'combination' of parameters than their analogous 'normal' stem cells or may produce different cellular response if use the same combination of parameters. Using various methods of photomodulation or other techniques known in the art more specific cellular effects may be produced by 'blocking' some 'channels' that are photomodulated.

For example, consider an old fashioned juke box, if one selects the proper buttons one will set in motion a series of events resulting in the playing of a very specific and unique record or song. If however one were given a broom to push the buttons one would have to block all but the desired button to be selective. Likewise pushing an immediately adjacent button will not produce the desired outcome.

The magnitude of effects on cells may also be very dependent on the wavelength (when other parameters are the same). One such example is the contrast between irradiating chemical bonds in DNA with 302 nm light versus 365 nm light—the 302 nm light produces approximately 5000 times greater DNA pyrimidine dimers than the 365 nm only a short distance up the spectrum. Changing the wavelength can also convert the ratio or type of these dimers. Thus seemingly subtle changes in photomodulation or photochemical reaction parameters can produce very large and very significant differences in cellular effects—even at the subcellular level or with DNA or gene expression.

A final analogy is that photo modulation parameters can be much like a "morse code" to communicate specific 'einstructions' to stem cells. This has enormous potential in practical terms such as guiding or directing the type of cells, tissues or organs that stem cells develop or differentiate into as well as stimulating, enhancing or accelerating their growth (or keeping them undifferentiated).

Another application of photomodulation is in the treatment of cellulite. Cellulite is a common condition which represents a certain outward appearance of the skin in certain anatomic areas—most commonly on the upper legs and hips which is widely regarded as cosmetically undesirable. Cellulite is the result of a certain anatomic configuration of the skin and underlying soft tissues and fat which may involve abnormalities of circulation or microcirculation or metabolic abnormalities—predominantly in the fat and supporting tissues. Photomodulation or photothermal treatments of the adipocytes (fat cells) or their surrounding supporting structures and blood supply alone or in combination can reduce the appearance of cellulite and/or normalize the structure and function of the tissues involved with the cellulite.

Photomodulation of adipocytes can be performed using endogenous chromophores such as the adipocytes themselves, their mitochondria or other targets within the adipocyte electron transport system or respiratory chain or other subcellular components. Exogenous light or electromagnetically activated chromophores can also be photomodulated (photoactivated or photoinhibited) or photothermal interactions can also occur. Examples of such chromophores are listed elsewhere in this application and can be topically or systemically introduced into the target tissues or adipocytes or surrounding blood vessels. The use of externally or internally applied ultrasound can be utilized either to enhance delivery of the chromophore or to alter local circulation or to provide thermal effect or to provide destructive effect or any combination of these actions.

In one embodiment the chromophore is delivered into the fat layer under the skin on the thigh using external ultrasound to enhance skin permeability and also enhance transport. The alteration of the stratum corneum alone or in combination with the ultrasound can further enhance delivery of the chromophore. External massage therapy from various techniques can be used to enhance the treatment process. In another embodiment chromophore is injected into the fat layer prior o treatment with light. Some light therapy with or without ultrasound may be used to photomodulate or photothermally or ultrasonically increase or otherwise alter the circulation or microciruclation or local metabolic processes in the areas affected by cellulite or other tissues. The proper light parameters are selected for the target adipocytes, blood vessels, exogenous chromophores, etc. Since some of the target tissues in cellulite are deeper than for example wrinkles or acne, typically long enough wavelengths of light must be utilized so that the light penetrated deeply enough to reach the target tissue.

Various topical or systemic agents can also be used to enhance the cellulite reduction treatments. Some of these include various cofactors for the metabolic or adipocyte interactions described and have been previously described herein.

Additional topical agents for inhibiting hair growth include inhibitors of ornithine decarboxylase, inhibitors of vascular endothelial growth factor (VEGF), inhibitors of phospholipase A2, inhibitors of S-adenosylmethionine. Specific examples of these, but not limited to, include licorice, licochalone A, genistein, soy isoflavones, phtyoestrogens, vitamin D and derivatives, analogs, conjugates, natural or synthetic versions or genetically engineered or altered or immunologic conjugates with these agents.

Also the same topical agents, exogenous light activated chromophores and treatments described from cellulite above also are hereby incorporated into methods for reducing the growth of hair. Increasing the circulation or microcirculation of the hair bearing skin may also be accomplished by simply producing vasodilation by any method know to those skilled in this art. Some examples of topical agents which might be used to create such vasodilation include, but are not limited to: capsicum, ginseng, niacinamide, minoxidil, etc.

The present invention is further illustrated by way of the following examples.

EXAMPLE 1

Acne Reduction—Continuous Treatment

A team of blinded expert graders viewing before and after photos of patients subjected to the non-ablative LILT ("Low Intensity Light Therapy") of the present invention score the global improvement of visible acne prominent in the facial area.

Six females are treated to reduce acne by, first, treating their skin with a topical composition containing about 2.5%, by weight copper chlorophyllin as the active ingredient. The treatment includes subjecting the target area of the patient's skin that has been treated with the topical composition to a filtered fluorescent light operated continuously and providing full-face coverage, i.e., the entire face of the patient is subjected to the light from the light source. Three treatments over 12 weeks to the entire face with at a light intensity of 11 milliwatts for 15 minutes per treatment session, resulting in a total energy exposure of 10.0 J/cm$^2$. Thermal injury is produced with blood vessels included among the target chromophores (but no skin wound care is needed). The average reduction in acne is shown in Table 1. The light source has a dominant emissive wavelength in the range of 410 nm to 420 nm and is centered at 415 nm.

TABLE 1

| Week/Value | Averaged Value of Reduction |
| --- | --- |
| 0 weeks | 0% |
| 4 weeks | 28% |
| 8 weeks | 56% |
| 12 weeks | 64% |

EXAMPLE 2

Acne Reduction—Pulsed Treatment

A team of blinded expert graders viewing before and after photos of patients subjected to the non-ablative LILT ("Low Intensity Light Therapy") of the present invention score the global improvement of visible acne on the facial area.

Six females are treated for acne by, first, contacting their skin once nightly for each night during the 2 weeks preceding the treatment session with a topical composition containing a mixture of 2.0% chlorophyll a, 2.0% chlorophyll b, and 5% carotenoids as the active ingredients. The laser diode treatment includes subjecting the target area of the patient's skin that has been treated with the topical composition to a laser diode light having a pulse width of 800 msec and a pulse frequency of 1 hz (1 pulse per second). Three pulses are administered. Six treatments over 12 weeks to the entire face with 400 nm laser diode with a 10 cm beam diameter at an intensity ranging 2500 milliwatts/cm2. The average reduction in acne is shown in Table 2.

TABLE 2

| Week/Value | Averaged Value of Reduction |
| --- | --- |
| 0 weeks | 0% |
| 2 weeks | 36% |
| 7 weeks | 58% |
| 12 weeks | 82% |

EXAMPLE 3

Acne and Acne Scarring Reduction Combined Continuous Wave/Pulsed Treatment

Three females showing active acne and acne scarring in the facial area are tested for improvement in scar prominence, skin texture, and scar visibility before and after receiving treatment in accordance with the non-ablative method of the present invention used in conjunction with a topical composition containing the active ingredient chlorophyll in a carrier suspension of microsponges having a diameter of 5 microns or less. Measurements are taken from by utilizing subjective evaluations conducted by trained medical personnel. The topical treatment includes applying the carotenoid composition containing about 5% carotenoids in a liposome carrier (alternatively, microsponges can be used having an average diameter of 5 microns) to the skin of the facial area and allowing it to penetrate the stratum corneum for approximately 15-20 minutes prior to beginning treatment. The first step in the treatment process is to expose the facial area to a continuos wave from a filtered metal halide lamp having a dominant emissive wavelength, i.e., an emission peak, at about 415 nm+/−5 nm and an energy output of 100 mW/cm$^2$ for approximately 10 minutes. The patient's facial area is then exposed to a pulsed LED treatment includes subjecting the target chromophore fibroblasts and subcellular components thereof to LED light having a pulse width of 250 msec and a pulse spacing of 250 msec for 90 pulses. Six treatments over 12 weeks to the entire face with the metal halide source as previously described and a 590 nm multichromatic LED, i.e., an LED having an emission peak at about 590 nm and putting out medically useful light in the range of about 585 nm to about 595 nm, at an intensity ranging from 1.05-2.05 µWatts. Further, the treatment maintains a skin temperature below the threshold of thermal injury. The average improvement in acne scar visibility is shown in Table 3. In accordance with the present invention, this dual-source treatment method employs the metal-halide light source to treat the active acne and the LED source to reduce or eliminate the visibility of acne scars.

TABLE 3

| Percent Improvement | Pre treatments | Post treatments (%) |
|---|---|---|
| Skin Elasticity | 0 | 85 |
| Scarring | 0 | 46 |
| Active Acne Lesions | 0 | 79 |

EXAMPLE 4

Acne Scar Reduction—Pulsed Treatment

A team of blinded expert graders viewing before and after photos of patients subjected to the non-ablative LILT ("Low Intensity Light Therapy") of the present invention score the global improvement of visible acne scarring.

Six females were tested for reduction of acne scar visibility. The LED treatment includes subjecting the patient's skin to a LED light having a pulse width of 250 msec and a pulse spacing of 250 msec for a period of 90 pulses. Eight treatments over 16 weeks to the entire face with 590 nm multichromatic LED at an intensity ranging from 1.0-2.0 µWatts. Having a bandwidth of +/−5-15 nm, the LED therefore produces light in the wavelength range of from 575 nm to 605 nm. Further, the treatment maintains a skin temperature below the threshold of thermal injury. The average reduction in visible acne scarring is shown in Table 4.

TABLE 4

| Week/Value | Averaged Value of Reduction |
|---|---|
| 0 weeks | 0% |
| 4 weeks | 42% |
| 8 weeks | 51% |
| 12 weeks | 48% |

EXAMPLE 5

Acne Reduction—Continuous Light

A method for preventing or treating acne by a combination of photothermal and photomodulatory treatment is used to reduce the presence of acne bacteria, resulting in a substantial reduction in the existence of acne on the facial area. In this example, dual chromophores are targeted. A native, naturally occurring porphyrin in acne and an exogenous chromophor.

Pretreatment is performed using a topically applied chromophore. In this example, the topical chromophor is an aqueous solution of Na Cu Chlorophyllin and carotenoids is applied to the skin. The skin is first cleansed with a low residue cleansing solution, then a pH adjusting astringent lotion is applied by a 5-10 minute application of an enzyme mask for removing skin debris and a portion of the stratum corneum. The topical chromophore is applied and delivery of the chromophore is enhanced with a 3 megahertz ultrasound emitter using a duty cycle of 25% and 1.5 watts output using a massage-like motion to cover the entire face for 5 minutes and the shoulders for 5 minutes. Any excess lotion is then removed. The cleansing solution used for this example should include at least 40% of either an acetone, ethyl acetate, or ethyl/isopropyl alcohol solvent, from about 1% to about 4% salicylic acid as a penetrant enhancer, and about 5% glycerin, included as a moisturizer.

A filtered fluorescent light source having a dominant emission at 420 nm is set to emit continuously for 20 minutes at an intensity of 10 Joules/cm$^2$. The entire face and upper back of the patient is treated with minimal overlap during each of 6 treatment sessions, each spaced two week apart. Approximately an 85% reduction in acne is observed.

EXAMPLE 6

Home-Use Device and Treatment

The prevention or treatment method of Example 5 is carried out. The patient continues the treatment at home using a home-use device comprising a hand-held LED device, a lotion containing an aqueous solution of about 2%, by weight, chlorophyll and about 2%, by weight, of a carotenoid, and a wavelength selective sunscreen.

The patient applies a chlorophyll-containing topical solution to the areas previously treated for acne scarring once per day, preferably but not necessarily in the morning. Further, the patient applies a sunscreen typical of those known in the art except that it is formulated to permit the passage of radiation having a wavelength in the range of about 400 nm to about 420 nm and 600 nm to about 660 nm to allow natural sunlight to further aid the treatment process. The carotenoids provide protection to the skin against damage from ultraviolet radiation received from sunlight. Finally, the patient uses the hand-held LED device 1-2 times per day. The LED device emits radiation having a dominant emission at about 644 nm+/−5 nm at an energy output of approximately 20 micro-watts in a continuous wave. Each treatment session covers active acne lesions for acne lesions for approximately 2 minutes. A further reduction in the visibility of acne scarring is observed. Additional improvement in acne scar reduction can be achieved using a 590 nm multichromatic LED at an intensity ranging from 1.0-2.0 μWatts as described in prior examples.

EXAMPLE 7

Mixed Led Panel Treatment Array

An LED array includes both blue LEDs having a dominant emission at 415 nm to treat active acne and yellow LEDs having a dominant emission at 590 nm to prevent or treat acne scarring. The skin is pretreated in the same manner as described in Example 5. The LED array is then positioned to cover the entire facial area of the patient with a 20 minute continuous wave of blue light (415 nm) and an exposure of yellow (590 nm) light pulsed on for 250 milliseconds and off for 250 milliseconds. Approximately 100 pulses are delivered.

EXAMPLE 8

Sebaceous Gland Size Reduction

Female skin exhibiting active acne rosacea and numerous sebaceoushyperplasia lesions is treated with a metal halide light source having a dominant emission centered at 415 nm+/−5 nm and an energy output of 100 mW/cm$^2$ for approximately 10 minutes after having been treated with a topically applied composition containing chlorophyll and carotenoids as the active ingredients. A mixture of 2.0% chlorophyll a and b, 6.0% carotenoids (carotenses and xanthophylls) and 1.5% phycobilin is used. All percentages are by weight. Three treatments are administered at two-week intervals. Visual inspection shows a reduction in sebaceous gland size of 40%-60%.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

I claim:

1. An acne prevention method comprising:
exposing tissue to a first light source, the first light source comprising light emitting diodes emitting light at a wavelength of from about 300 nm to about 1300 nm and a total energy fluence of less than 4 J/cm$^2$; and applying a topical chromophore composition to the tissue either before or after exposing the tissue to electromagnetic radiation to prevent acne, wherein the topical chromophore composition has at least one absorption maximum between 300 nm and 1300 nm and comprises an active ingredient selected from the group consisting of chlorophyll, porphyrin, and combinations thereof, wherein the active ingredient has at least one metal-ligand bond, wherein the metal in the metal-ligand bond is selected from the group consisting of Fe, Mg, Cu, Al, reactive transition metals, metal chelates, and antibody complexes.

2. The method of claim 1, wherein the first light source delivers an energy fluence of less than 4 J/cm$^2$ via a continuous wave having a wavelength of from about 400 nm to about 490 nm.

3. The method of claim 1, wherein the first light source delivers an energy fluence of less than 4 J/cm$^2$ via a continuous wave having a wavelength of from about 560 nm to about 600 nm.

4. The method of claim 1, wherein the first light source delivers an energy fluence of less than 4 J/cm$^2$ via a continuous wave having a wavelength of from about 600 nm to about 650 nm.

5. The method of claim 1, wherein the first light source delivers an energy fluence of less than 4 J/cm$^2$ via a continuous wave having a wavelength of from about 790 nm to about 850 nm.

6. The method of claim 1, wherein the first light source delivers an energy fluence of less than 4 J/cm$^2$ via a series of pulses of light having a wavelength of from about 400 nm to about 490 nm.

7. The method of claim 1, wherein the first light source delivers an energy fluence of less than 4 J/cm$^2$ via a series of pulses of light having a wavelength of from about 560 nm to about 600 nm.

8. The method of claim 1, wherein the first light source delivers an energy fluence of less than 4 J/cm$^2$ via a series of pulses of light having a wavelength of from about 600 nm to about 650 nm.

9. The method of claim 1, wherein the first light source delivers an energy fluence of less than 4 J/cm$^2$ via a series of pulses of light having a wavelength of from about 790 nm to about 850 nm.

* * * * *

UNITED STATES PATENT AND TRADEMARK OFFICE
CERTIFICATE OF CORRECTION

| | | |
|---|---|---|
| PATENT NO. | : 7,494,503 B2 | Page 1 of 1 |
| APPLICATION NO. | : 11/783538 | |
| DATED | : February 24, 2009 | |
| INVENTOR(S) | : David H. McDaniel | |

It is certified that error appears in the above-identified patent and that said Letters Patent is hereby corrected as shown below:

In column 13, lines 55 - 58, please replace the sentence:

"For purposes of the present invention, any device that emits electromagnetic radiation in a bandwidth of +/- about 1000 nanometers around a dominant wavelength can be considered to be a narrowband, multichromatic emitter."

with the following sentence:

"For purposes of the present invention, any device that emits electromagnetic radiation in a bandwidth of +/- about 100 nanometers around a dominant wavelength can be considered to be a narrowband, multichromatic emitter."

Signed and Sealed this
Eighth Day of November, 2011

David J. Kappos
*Director of the United States Patent and Trademark Office*